United States Patent [19]

Qvist et al.

[11] Patent Number: 6,110,689
[45] Date of Patent: *Aug. 29, 2000

[54] METHOD OF ASSAYING COLLAGEN FRAGMENTS IN BODY FLUIDS, A TEST KIT AND MEANS FOR CARRYING OUT THE METHOD AND USE OF THE METHOD TO DIAGNOSE THE PRESENCE OF DISORDERS ASSOCIATED WITH THE METABOLISM OF COLLAGEN

[75] Inventors: Per Qvist, Klampenborg; Martin Bonde, Lyngby, both of Denmark

[73] Assignee: Osteometer A/S, Rodovre, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/963,825

[22] Filed: Nov. 4, 1997

Related U.S. Application Data

[63] Continuation of application No. 08/187,319, Jan. 21, 1994, abandoned.

[51] Int. Cl.$^7$ .................................................. G01N 33/53
[52] U.S. Cl. ...................... 435/7.1; 435/7.93; 435/7.94; 435/70.21; 435/331; 435/975; 436/518; 436/536; 436/548; 436/815; 530/300; 530/323; 530/328; 530/387.9; 530/388.1; 530/391.1; 530/391.3
[58] Field of Search .............................. 435/7.93, 7.94, 435/70.21, 240.37, 975, 7.1, 331; 436/518, 536, 548, 803, 815; 530/300, 323, 328, 329, 330, 387.1, 388.1, 391.1, 391.3, 387.9

[56] References Cited

U.S. PATENT DOCUMENTS

| | | | |
|---|---|---|---|
| 3,600,132 | 8/1971 | Goverde | 436/90 |
| 4,312,853 | 1/1982 | Timpl | 436/540 |
| 4,504,587 | 3/1985 | Timpl et al. | 436/538 |
| 4,628,027 | 12/1986 | Gay . | |
| 4,778,768 | 10/1988 | Heinegard et al. | 436/501 |
| 5,300,434 | 4/1994 | Eyre . | |
| 5,320,970 | 6/1994 | Eyre . | |
| 5,455,179 | 10/1995 | Eyre . | |
| 5,472,884 | 12/1995 | Eyre . | |
| 5,473,052 | 12/1995 | Eyre . | |
| 5,532,169 | 7/1996 | Eyre . | |
| 5,576,189 | 11/1996 | Eyre . | |
| 5,607,862 | 3/1997 | Eyre . | |
| 5,641,687 | 6/1997 | Eyre | 436/518 |
| 5,641,837 | 6/1997 | Eyre | 435/7.1 |
| 5,652,112 | 7/1997 | Eyre | 435/7.1 |
| 5,656,439 | 8/1997 | Eyre | 435/7.1 |
| 5,753,450 | 5/1998 | Baylink | 435/7.93 |

FOREIGN PATENT DOCUMENTS

| | | |
|---|---|---|
| 0 394 296 B1 | 10/1990 | European Pat. Off. . |
| 0 424 428 B1 | 5/1991 | European Pat. Off. . |
| 0 502 928 B1 | 9/1992 | European Pat. Off. . |
| A2 0505210 | 9/1992 | European Pat. Off. . |
| 2 205 643 | 5/1987 | United Kingdom . |
| WO 83/04104 | 11/1983 | WIPO . |
| WO 88 08980 WO A1 | 11/1988 | WIPO . |
| 8904491 WO A1 | 5/1989 | WIPO . |
| 8912824 | 12/1989 | WIPO . |
| WO 90 04417 WO A1 | 5/1990 | WIPO . |
| 9108478 | 6/1991 | WIPO . |
| WO 92/21698 | 12/1992 | WIPO . |
| WO 94/14844 | 7/1994 | WIPO . |
| WO 95/04282 | 2/1995 | WIPO . |

OTHER PUBLICATIONS

Harlow et al., "Antibodies—A Laboratory Manual", Cold Spring Harbor, (1988), pp. 72–77.
Delmas et al., "Biochemical Markers of Bone Turnover for the Clinical Assessment of Metabolic Bone Disease", *Endocrinology and Metabolism Clinics of North America*, vol. 19, No. 1, (1990), pp. 1–18.
Mintz et al., "Detection of Procollagen Biosynthesis Using Peptide–Specific Antibodies," *Matrix*, vol. 10, No. 3, pp. 186–199 (1990).
Schroter–Kermani, C. et al., *Immunol Invest* 19(5–6);475–91, Oct.–Dec. 1990.
Otter, A. et al., *J. Biomol. Struct. Dyn.*, 7(3):455–76, Dec. 1989.
Werkmeister, J.A. et al. *Eur J Biochem* 187(2):439–43, Jan. 26, 1990.
Delmas PD et al., J Bone Min. Res, 1:333–337 (1986).
Loidl et al., Nucleic Acids Research, 12:9383–9394 (1984).
Sangiorgi et al., *Nucleic Acids Research,* 13:2207–2225 (1985).
Baldwin et al., Biochem J, 262:521–528 (1989).
Ala–Kokko et al., Biochem J, 260:509–516 (1989).
Kühn K, in Immunochemistry of the Extracellular Matrix, 1:1–29, CRC Press, Inc., Boca Raton, Florida (1982).
Eyre DR, Ann.Rev.Biochem, 53:717–748 (1984).
Singer FR et al., Metabolic Bone Disease, vol. II (eds. Avioli LV and Kane SM), 489–575 (1978), Academic Press, New York.

(List continued on next page.)

*Primary Examiner*—Jeffrey Stucker
*Attorney, Agent, or Firm*—Pennie & Edmonds LLP

[57] ABSTRACT

A method of assaying collagen fragments in body fluids, including bringing a sample of body fluid in contact with at least one immunological binding partner for the collagen fragments, said binding partner being immunoreactive with synthetic peptides, the sequences of which are essentially derived from collagen and containing potential sites for cross-linking. The immunological binding partners are incorporated, either as whole antibodies or as immunologically active fragments thereof, in an assay for quantitative determination of collagen fragments in the sample. In addition to being contacted with the immunological binding partner(s), the sample may be brought into direct contact with the corresponding synthetic peptide. The invention further comprises a test kit and specific means for carrying out the method. The structure of specific peptides is also described.

13 Claims, 7 Drawing Sheets

OTHER PUBLICATIONS

Russell et al., Metab. Bone Dis. and Rel. Res. 4 and 5, 225–262 (1981).
Kiviriko KI, Int.Rev.Connect.Tissue Res, 5:93 (1979).
Weiss PH and Klein L, J Clin Invest, 48:1 (1969).
Wu and Eyre, Biochemistry, 23:1850 (1984).
Black et al., Annals of the Rheumatic Diseases, 48:641–644 (1989).
Robins et al., Annals of the Rheumatic Diseases, 45:969–973 (1986).
Seibel et al., The Journal of Dermatology, 16:964 (1989).
Hanson et al., Journal of Bone and Mineral Research, 7:1251–1258 (1992).
Pierard et al., Analytical Biochemistry, 141:127–136 (1984).
Niemela, Clin.Chem., 31/8:1301–1304 (1985).
Rohde et al., European Journal of Clinical Investigation, 9:451–459 (1979).
Dodge, J. Clin.Invest, 83:647–661 (1981).
Campell AM, Laboratory Techniques in Biochemistry and Molecular Biology, vol. 13 (1986), pp. 66–165.
Morein B et al., Nature, 308:457–460 (1984).
Goding JW, in Monoclonal Antibodies: Principles and Practice (1986), pp. 59–103.
Ishikawa E, Journal of Immunoassay, 3:209–327 (1983).
Uebelhart D, Bone and Mineral, 8:87–96 (1990).
Chu ML, de Wet W, Bernard M, Ding JF, Morabito M, Myers J, Williams C, and Ramirez F, Nature, 310:337–340 (1984).
Click EM and Bornstein P, Biochemistry, 9:4699–4706 (1970).
Morgan PH, Jacobs HG, Segrest JP, and Cunningham LW, J.Biol.Chem., 245:5042–5048 (1970).
Bernard MP, Chu ML, Myers JC, Ramirez F, Eikenberry EF, and Prockop DJ, Biochemistry, 22:5213–5223 (1983).
de Wet W, Bernard M, Benson–Chanda V, Chu ML, Dickson L, Weil D, and Ramirez F, J.Biol.Chem, 262:16032–16036 (1987).
Su MW, Lee B, Ramirez F, Machado M, Horton W, Nucleic Acids Res, 17:9473 (1989).
Ala–Kokko L, Baldwin CT, Moskowitz RW, and Prockop DJ, Proc.Natl.Acad.Sci, 87:6565–6568 (1990).
Vikkula M and Peltonen L, FEBS Lett, 250:171–174 (1989).
Janeczko RA and Ramirez F, Nucleic Acids Res, 17:6742 (1989).
Beardsworth et al., 1990, "Changes with age in the urinary excretion of lysyl– and hydroxylysylpyridinoline, two new markers of bone collagen turnover", *J. Bone Miner. Res.* 5:671–676.
Black et al., 1988, "Quantitative analysis of the pyridinium crosslinks of collagen in urine using ion–paired reversed–phase high–performance liquid chromatography", *Ana. Biochem.* 169:197–203.
del Pozo et al., 1986, "Binding of 1–anilinophthalene–8–sulfonic acid to type I collagen" *Int. J. Pept. Protein Res.* 28:173–178.
P.D. Delmas, 1990, "Biochemical markers of bone turnover for the clinical assessment of metabolic bone disease", *Metabolic Bone Dis.* 19:1–18.
Dickson et al., 1993, "Pyridonolines and cross–linked type I collagen N–telopeptides as markers of bone metastases in breast cancer" 15th Annual Mtg of the Amer Soc for Bone.
Eyre et al., 1988, "Identification of urinary peptides derived from cross–linking sites in bone collagen in Paget's disease", *J. of Bone & Mineral Res* 3:S210, Abst.565.
D.R. Eyre, 1994, "New molecular markers of bone metabolism", Ther. Res. (Symposium) 15:532–535.
D. Fujimoto, 1980, "Evidence for natural existence of pyridinoline crosslink in collagen", *Biochem & Biophys. Res. Comm.* 93:948–953.
Fujimoto et al., 1983, "Analysis of pyridinoline, a cross–linking compound of collagen fibers, in human urine", *J. Biochem.* 94:1133–1136.
H. Furthmayr, 1982, "Immunization procedures, isolation by affinity chromatography, and serological and immunochemical characterization of collagen specific antibodies", *Immunochemistry of the extracellular matrix,* H. Furthmayr (ed.), CRC Press, vol. 1, Chap. 11, pp. 143–178.
Gertz et al., 1994, "Monitoring bone resorption in early postmenopausal women by an immunoassay for cross–linked collagen peptides in urine", *J. of Bone & Min. Res.* 9:135–142.
Gunja–Smith & Boucek, 1981 "Collagen cross–linking compounds in human urine", *Biochem. J.* 197:759–762.
Hanson et al., 1992, "A specific immunoassay for monitoring human bone resorption: Quantitation of type I collagen cross–linked N–telopeptides in urine", *J. of Bone & Min. Res.* 7:1251–1258.
Hassager et al., 1994, "The carboxy–terminal pyridinoline cross–linked telopeptide of type I collagen in serum as a marker of bone resorption: The effect of nandrolone decanoate and hormone replacement therapy", *Calcif. Tissue Int.* 54:30–33.
Henkel et al., 1987, "Characterization of type–I collagen trimeric cross–linked peptide from calf aorta and its cross–linked structure", *Eur. J. Biochem.* 165:427–436.
Kruger–Franke, 1991, "Pyridinoline–containing collagen degradation products in the urine of patients with osteoarthrosis of the hip joint", *Z. Rheumatol.* 50:323–327 (German with English Translation).
Kuboki et al., 1981, "Location of the intermolecular cross–links in bovine dentin collagen, solubilization with trypsin and isolation of cross–link peptides containing dihydroxylysinonorleucine and pyridinoline", *Biochem. & Biophys. Res. Comm.* 102:119–126.
K. Kuhn, 1982, "Chemical properties of collagen", *Immunochemistry of the Extracellular Matrix,* H. Furthmayr (ed.), CRC Press, vol. 1, Chap. 1, pp. 1–23.
K. Kuhn, 1987, "The classical collagens: Types I, II, and III", *Structure & Function of Collagen Types,* Mayne & Bergeson (eds.), Academic Press, Chap 1, pp. 10–23.
Kuypers et al., 1992, "Identification of the loci of the collagen–associated Ehrlich chromogen in type I collagen confirms its role as a trivalent cross–link", *Biochem. J.* 282:129–136.
Macek & Adam, 1987, "Determination of collagen degradation products in human urine in osteoarthrosis", *Z. Rheumatol.* 46:237–240.
Otter et al., 1988, "Type I collagen α–1 chain c–telopeptide: Solution structure determined by 600–MHZ proton NMR spectroscopy and implications for its role in collagen fibrillogenesis", *Biochem.* 27:3560–3567.
Rennard et al., 1980, "Enzyme–linked immunoassay (ELISA) for connective tissue components", *Anal. Biochem.* 104:205–214.
Risteli & Risteli, 1986, "Radioimmunoassay for monitoring connective tissue metabolism", *Rheumatol.* 10:216–245.

Risteli et al., 1993, "Radioimmunoassay for the pyridinoline cross–linked carboxy–terminal telopeptide of type I collagen: A new serum marker of bone collagen degradation", *Clin. Chem.* 39:635–640.

S.P. Robins, 1982, "An enzyme–linked immunoassay for the collagen cross–link pyridinoline", *Biochem J.* 207:617–620.

Robins et al., 1987, "Measurement of hydroxypyridinium crosslinks of collagen as an index of bone matrix degradation", Paper, Lake Garda, Italy, p. 23, Abstr. OP45.

Rodriguiz et al., 1993, "Type I Collagen cross–linked N–telopeptide be osteopetrotic patients during interferon gamma therapy: A correlation with bone biochemical and densitometric markers", 15$^{th}$ Annual Mtg of the Amer. Soc. for Bone & Min. Res., Tampa, Fl., Sep., 8:S291, Abstr. 698.

Rohde et al., 1983, "Serum and urine analysis of the aminoterminal procollagen peptide type III by radioimmunoassay with antibody fab fragments", *Collagen Rel. Res.* 3:371–379.

Schuppan et al., 1986, "Radioimmunoassay for the carboxy–terminal cross–linking domain of type IV (basement membrane) procollagen in body fluids", *J. Clin. Invest.* 78:241–248.

P.G. Scott, 1986, "Spectropic study of environment–dependent changes in the confirmation of the isolated carboxy–terminal telopeptide of type I collagen", *Biochem.* 25:974–980.

Tellerova et al., 1986, "Determination of larger urinary peptides in osteoarthrosis by high–performance liquid chromatography", *Scand. J. Rheumatol.* 15:52–56.

Eyre et al., 1984, "Quantitation of Hydroxypyridinium Crosslinks in Collagen by High–Performance Liquid Chromatography", *Analytical Biochemistry* 137:380.

METHOD OF ASSAYING COLLAGEN FRAGMENTS IN BODY FLUIDS, A TEST KIT AND MEANS FOR CARRYING OUT THE METHOD AND USE OF THE METHOD TO DIAGNOSE THE PRESENCE OF DISORDERS ASSOCIATED WITH THE METABOLISM OF COLLAGEN

This is a continuation of application Ser. No. 08/187,319, filed Jan. 21, 1994, now abandoned.

The present invention relates to a method of determining collagen fragments in body fluids. The invention further relates to means, including synthetic peptides, monoclonal and polyclonal antibodies and cell lines, for use in carrying out the method of the invention. Still further, the invention relates to the use of the above method to diagnose the presence of disorders associated with the metabolism of collagen, especially osteoporosis.

BACKGROUND OF THE INVENTION

Collagens and Disorders of Collagen Metabolism

Osteoporosis is the most common bone disease in humans. Primary osteoporosis, accompanied by increased susceptibility to fractures, results from a progressive reduction in skeletal bone mass. It is estimated to affect 15–20 million individuals in the USA alone. Its basis is an age-dependent imbalance in bone remodeling, i.e., in the rates of formation and resorption of bone tissue.

In the USA about 1.2 million osteoporosis-related fractures occur in the elderly each year including about 538,000 compression fractures of the spine, about 227,000 hip fractures and a substantial number of early fractured peripheral bones. Between 12 and 20% of the hip fractures are fatal because they cause severe trauma and bleeding, and half of the surviving patients require nursing home care. Total costs from osteoporosis-related injuries now amount to at least $10 billion annually in the USA (Riggs, *New England Journal of Medicine* 327:620–627 (1992)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, the availability of reliable assays for measuring bone resorption rates in patients or in healthy subjects is very limited. Other disorders entailing (and correlated with) abnormalities in collagen metabolism include Paget's disease, Marfan's syndrome, osteogenesis imperfecta neoplastic growth in collagenous tissue, dwarfism, rheumatoid arthritis, osteoarthritis and vasculitis syndrome.

Three known classes of human collagen have been described to date. The Class I collagens, subdivided into types I, II, III, V, and XI, are known to form fibrils. Their full amino-acid sequence (to the extent they have been elucidated) are attached in Appendix A.

Collagen type I accounts for more than 90% of the organic matrix of bone. Therefore, in principle, it is possible to estimate the rate of bone resorption by monitoring the degradation of collagen type I. Likewise, a number of other disease states involving connective tissue can be monitored by determining the degradation of collagen. Examples are collagen type II degradation associated with rheumatoid arthritis and osteoarthritis and collagen type III degradation in vasculitis syndrome.

Amino acid sequences of human type III collagen, human pro 1(II) collagen, and the entire prepro 1(III) chain of human type III collagen and corresponding cDNA clones have been investigated and determined by several groups of researchers; see Loil et al., *Nucleic Acids Research* 12:9383–9394 (1984); Sangiorgi et al., *Nucleic Acids Research* 13:2207–2225 (1985); Baldwin et al., *Biochem J.* 262:521–528 (1989); and Ala-Kokko et al., *Biochem. J.* 260:509–516 (1989).

Type I, II, and III collagens are all formed in the organism as procollagen molecules, comprising N-terminal and C-terminal propeptide sequences, which are attached to the core collagen molecules. After removal of the propeptides, which occur naturally in vivo during collagen synthesis, the remaining core of the collagen molecules consists largely of a triple-helical domain having terminal telopeptide sequences which are non-triple-helical. These telopeptide sequences have an important function as sites of intermolecular cross-linking of collagen fibrils extracellularly. The alpha-helical region also includes crosslinkable sites. Peptides from this region are part of the present invention.

Intermolecular cross-links provide collagen fibrils with biomechanical stability. The formation of these cross-links is initiated by modification of lysine and hydroxylysine residues to the corresponding aldehydes. Several of these residues located on adjacent chains of collagen will spontaneously form different intermolecular cross-links. The exact position of the sites for cross-linking on collagen telopeptides and from the helical region has been previously described. See, for example, Kühn, K., in *Immunochemistry of the Extracellular Matrix* 1:1–29, CRC Press, Inc., Boca Raton, Fla. (1982), Eyre, D. R., *Ann. Rev. Biochem.* 53:717–48 (1984) or U.S. Pat. No. 5,140,103). Furthermore, the amino acid sequences of some potential sites for cross-linking in type I, II, and III collagen are given in Table 1 below.

The fibrous proteins, collagen and elastin, are cross-linked by a unique mechanism based on aldehyde formation from lysine or hydroxylysine side chains. Four homologous loci of cross-linking are evident in molecules of type I, II and III collagens (for review see Kühn, K., in *Immunochemistry of the Extracellular Matrix* 1:1–29 (1982)). Two are aldehyde sites, one in each telopeptide region. The other two sites are hydroxylysine symmetrically placed at about 90 residues from each end of the molecule. When collagen molecules pack into fibrils, these latter sites in the helical region align and react with telopeptide aldehydes in adjacent molecules. There is now strong evidence that 3-hydroxypyridinium residues are the mature cross-link coming from hydroxylysine-derived aldehydes. The mature cross-linking residues of the other pathway, i.e. from aldehyde formation of lysine residues, is, however, still unknown.

Prior Art Assays for Collagen Degradation

In the past, assays have been developed for monitoring degradation of collagen in vivo by measuring various biochemical markers, some of which have been degradation products of collagen. However, none of these methods are based upon the use of immunological binding partners in the form of antibodies which are immunoreactive with synthetic peptides having a sequence essentially derived from collagen fragments having crosslinkable sites.

For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as discussed further below.

For this reason, urinary hydroxyproline has been used extensively as an amino acid marker for collagen degradation; Singer, F. R. et al., *Metabolic Bone Disease, Vol. II* (eds. Avioli, L. V., and Kane, S. M.), 489–575 (1978), Academic Press, New York.

U.S. Pat. No. 3,600,132 discloses a process for the determination of hydroxyproline in body fluids such as serum, urine, lumbar fluid and other intercellular fluids in order to monitor deviations in collagen metabolism. The patent states that hydroxyproline correlates with increased collagen anabolism or catabolism associated with pathological conditions such as Paget's disease, Marfan's syndrome, osteogenesis imperfecta, neoplastic growth in collagen tissues and in various forms of dwarfism.

Bone resorption associated with Paget's disease has also been monitored by measuring small peptides containing hydroxyproline, which are excreted in the urine following degradation of bone collagen; Russell et al., *Metab. Bone Dis. and Rel. Res.* 4 and 5:255–262 (1981), and Singer, F. R., et al., supra.

In the case of Paget's disease, the increased urinary hydroxyproline probably comes largely from bone degradation; hydroxyproline, however, generally cannot be used as a specific index for bone degradation. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline.

Furthermore, about 80% of the free hydroxyproline derived from protein degradation is metabolized in the liver and never appears in the urine. Kiviriko, K. I., *Int. Rev. Connect. Tissue Res.* 5:93 (1970), and Weiss, P. H. and Klein, L., *J. Clin. Invest.* 48:1 (1969). Hydroxyproline is a good marker for osteoporosis, but it is troublesome to handle. It is specific for collagen in bones.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption; Krane, S. M. and Simon, L. S., *Develop. Biochem.* 22:185 (1981).

Other researchers have measured the cross-linking compound 3-hydroxypyridinium in urine as an index of collagen degradation in joint diseases. See, for background and as examples, Wu and Eyre, *Biochemistry* 23:1850 (1984); Black et al., *Annals of the Rheumatic Diseases* 48:641–644 (1989); Robins et al.; *Annals of the Rheumatic Diseases* 45:969–973 (1986); and Seibel et al., *The Journal of Dermatology* 16:964 (1989). In contrast to the present invention, these prior researchers have hydrolyzed peptides from body fluids and then looked for the presence of individual 3-hydroxypyridinium residues.

Assays for determination of the degradation of type I, II, and III collagen are disclosed in U.S. Pat. No. 4,973,666 and U.S. Pat. No. 5,140,103. However, both these patents are restricted to collagen fragments containing the cross-linker 3-hydroxypyridinium, whereas the present invention does not rely on the presence or absence of this particular cross-linking structure. Furthermore, the above-mentioned assays require tedious and complicated purifications from urine of collagen fragments containing 3-hydroxypyridinium to be used for the production of antibodies and for antigens in the assays.

At present very few clinical data using the approach described in U.S. Pat. No. 4,973,666 and U.S. Pat. No. 5,140,103 are available. Particularly, no data concerning the correlation between the urinary concentration (as determined by methods described in the above-mentioned patents) of 3-hydroxypyridinium containing telopeptides of type I collagen and the actual bone loss (as determined by repeated measurements by bone densitometry) are published. The presence of 3-hydroxypyridinium containing telopeptides in urine requires the proper formation in bone tissue of this specific cross-linking structure at various times before the bone resorbing process. Very little information on these processes is available and the present invention seeks to circumvent this dependance of the correct formation of the cross-linking structure. Furthermore, preliminary data indicate that in one embodiment of the present invention a major fraction of the molecules reactive in the assay has a molecular weight of more than 4,000 daltons. On the contrary, only molecules with a molecular weight below 2.000 daltons are identified in urine with the monoclonal antibody used in the assay; Hanson et al., *Journal of Bone and Mineral Research* 7:1251–1258 (1992). This demonstrates that the method according to the present invention has a very different profile of reactivities, i.e. it detects very different molecules, compared to methods described in the two above-mentioned U.S. patents.

None of the above researchers have reported specifically assaying a crosslinkable collagen fragment that is naturally produced in vivo upon collagen degradation, as in the present invention.

GB patent application No. 2,205,643 reports that the degradation of type III collagen in the body can be quantitatively determined by measuring the concentration of an N-terminal telopeptide from type III collagen in a body fluid. This method does not relate to methods employing antibodies reactive with specific, low molecular weight sequences around crosslinkable structures. Instead, the method uses antibodies generated to N-terminal telopeptides released by bacterial collagenase degradation of type III collagen, said telopeptides being labelled and used in the assay.

There are a number of reports indicating that collagen degradation can be measured by quantitating certain procollagen peptides. Propeptides are distinguished from telopeptides and alpha-helical region of the collagen core by their location in the procollagen molecule and the timing of their cleavage in vivo; see U.S. Pat. No. 4,504,587; U.S. Pat. No. 4,312,853; Pierard et al., *Analytical Biochemistry* 141:127–136 (1984); Niemela, *Clin. Chem.* 31/8:1301–1304 (1985); and Rohde et al., *European Journal of Clinical Investigation* 9:451–459 (1979).

U.S. Pat. No. 4,778,768 relates to a method of determining changes occurring in articular cartilage involving quantifying proteoglycan monomers or antigenic fragments thereof in a synovial fluid sample. This US patent does not relate to detecting collagen fragments derived from degraded collagen.

Dodge, *J. Clin, Invest.* 83:647–661 (1981) discloses methods for analyzing type II collagen degradation utilizing a polyclonal antiserum that specifically reacts with unwound alpha-chains and cyanogen bromide-derived peptides of human and bovine type II collagens. Contrary to the present invention the degradation products of collagen were not detected in a body fluid, but histochemically by staining of cell cultures, i.e. by "in situ" detection. The main difference between Dodge and the present invention is that Dodge measures type II collagen degradation in situ. By "in situ" is meant a determination carried out in the cells or tissue in which the degradation takes place. There is quite a fundamental difference between this determination and a method based upon tracing a marker in vitro, e.g. in the urine.

None of these references specify the structures of particular telopeptide or alpha-helical degradation products that could be measured to determine the amount of degraded fibrillar collagen in vivo.

SUMMARY OF THE INVENTION

The present invention is based on the discovery of the presence of particular collagen fragments in body fluids of patients and normal human subjects. The collagen fragments are generated upon collagen degradation and are partly characterized by the presence of potential sites for cross-linking, e.g. by the presence of lysine or hydroxylysine (Kühn, K., *Immunochemistry of the Extracellular Matrix* 1:1–29 (1982)). It is believed that a fraction of the collagen fragments measured by the assays embodied in the present invention are normally covalently linked in vivo to other peptide fragments through different, unidentified or already identified cross-links.

The method of the present invention may be used for determination of the degradation of human collagen of type I, II, and III.

The present invention provides a method of assessing the degradation of collagen based on a determination of the presence and quantity of a particular class of collagen fragments produced in vivo upon collagen degradation; and a comparison of the detected collagen fragments to those of a predetermined standard developed by measuring the same class of collagen fragments in normal individuals, i.e. individuals not afflicted with a disorder affecting collagen metabolism, said individuals being sex- and age-matched with the subjects being tested.

The present invention uses antibodies immunoreactive with synthetic peptides without these cross-linking structures. Accordingly, it is believed that collagen fragments (corresponding to the synthetic peptides) with or without actual cross-links, but with crosslinkable sites, are measured in the assays embodied in the present invention.

In a preferred embodiment, the method is based on the competitive binding of collagen fragments in body fluids and of synthetic peptides essentially derived from collagen to immunological binding partners.

The present invention provides new and very simple procedures for the detection (qualitative and quantitative) of collagen fragments generated upon collagen degradation.

For purposes of the present invention, as disclosed and claimed herein, the following terms are as defined below:

"Antibody": A monoclonal or polyclonal antibody or immunoreactive fragment thereof (i.e. capable of binding the same antigenic determinant), including—but not limited to—Fab, Fab', and F(ab')2 fragments.

"Crosslinkable sites": loci in collagen telopeptide or helix amino acid sequences containing lysine or hydroxylysine residues which can form cross-links with telopeptides or helical amino acid sequences of other collagen molecules in vivo.

"Crosslinkable peptides": peptides containing a fragment of the collagen sequence including at least one crosslinkable site.

Test kit: A combination of reagents and instructions for use in conducting an assay.

"Essentially derived" (about structures): Structures with similar antigenicity, i.e. with an ability, above the level of a non-related peptide, to inhibit the binding of any of the mentioned synthetic peptides to an antibody immunoreactive with said synthetic peptide.

It is contemplated that the method may also be used for assaying collagen fragments in animal body fluids, e.g. for determination of the collagen metabolism. It also can be used during clinical testing of new drugs to assess the impact of these drugs on collagen metabolism.

More specifically, the present invention relates to methods for assaying collagen fragments by the use of synthetic peptides corresponding to the above-mentioned sequences of collagen. Generally, these synthetic peptides will have fewer amino acid residues than the entire collagen molecule, often they will have fewer than 10 amino acids. Also, the synthetic peptides, corresponding to molecules present in body fluids, e.g. urine, will have potential sites for cross-linking, preferably lysine or hydroxylysine, incorporated in the structure.

The present invention comprises the determination of collagen fragments by the use of antibodies which are immunoreactive with the above-mentioned synthetic peptides, said peptides each having a sequence derived from collagen fragments having crosslinkable sites.

The invention also includes cell lines (e.g. hybridomas) that produce monoclonal antibodies immunoreactive with the above-mentioned synthetic peptides. The invention further includes monoclonal antibodies produced by the fused cell hybrids, and those antibodies (as well as binding fragments thereof, e.g. Fab) coupled to a detectable marker. Examples of detectable markers include, but are not limited to, enzymes, chromophores, fluorophores, coenzymes, enzyme inhibitors, chemiluminescent materials, paramagnetic metals, spin labels and radioisotopes.

The methods of the invention involve quantitating in a body fluid the concentration of particular collagen fragments derived from collagen degradation. In a representative assay, collagen fragments in the patient's body fluid and a synthetic peptide immobilized on a solid surface are contacted with an immunological binding partner which is immunoreactive with the synthetic peptide. Suitable body fluids are e.g. human urine, blood, serum, plasma and synovial fluid. It is contemplated that the method may also be used e.g. on saliva and sweat. The body fluid may be used as it is, or it may be purified prior to the contacting step. This purification step may be accomplished using a number of standard procedures, including, but not limited to, cartridge adsorption and elution, molecular sieve chromatography, dialysis, ion exchange, alumina chromatography, hydroxyapatite chromatography, and combinations thereof.

The present invention is based on the discovery of simple procedures for quantitation of collagen fragments in body fluids. In a representative procedure, synthetic peptides containing potential sites for cross-linking, are used for the raising of antibodies and subsequently incorporated in the assay for quantitation of collagen fragments generated in vivo by collagen degradation.

The invention also includes test kits useful for quantitating in a body fluid the amount of collagen fragment derived from the degradation of collagen. The kits comprise at least one immunological binding partner, e.g. a monoclonal or polyclonal antibody specific for a peptide derived from the degradation of collagen. If desired, the immunological binding partner of the test kit may be coupled to detectable markers such as the ones described above.

The invention is described in more detail below. Reference is made to the appended drawings.

DETAILED DESCRIPTION AND BEST MODE OF CARRYING OUT THE INVENTION

Figure 1:
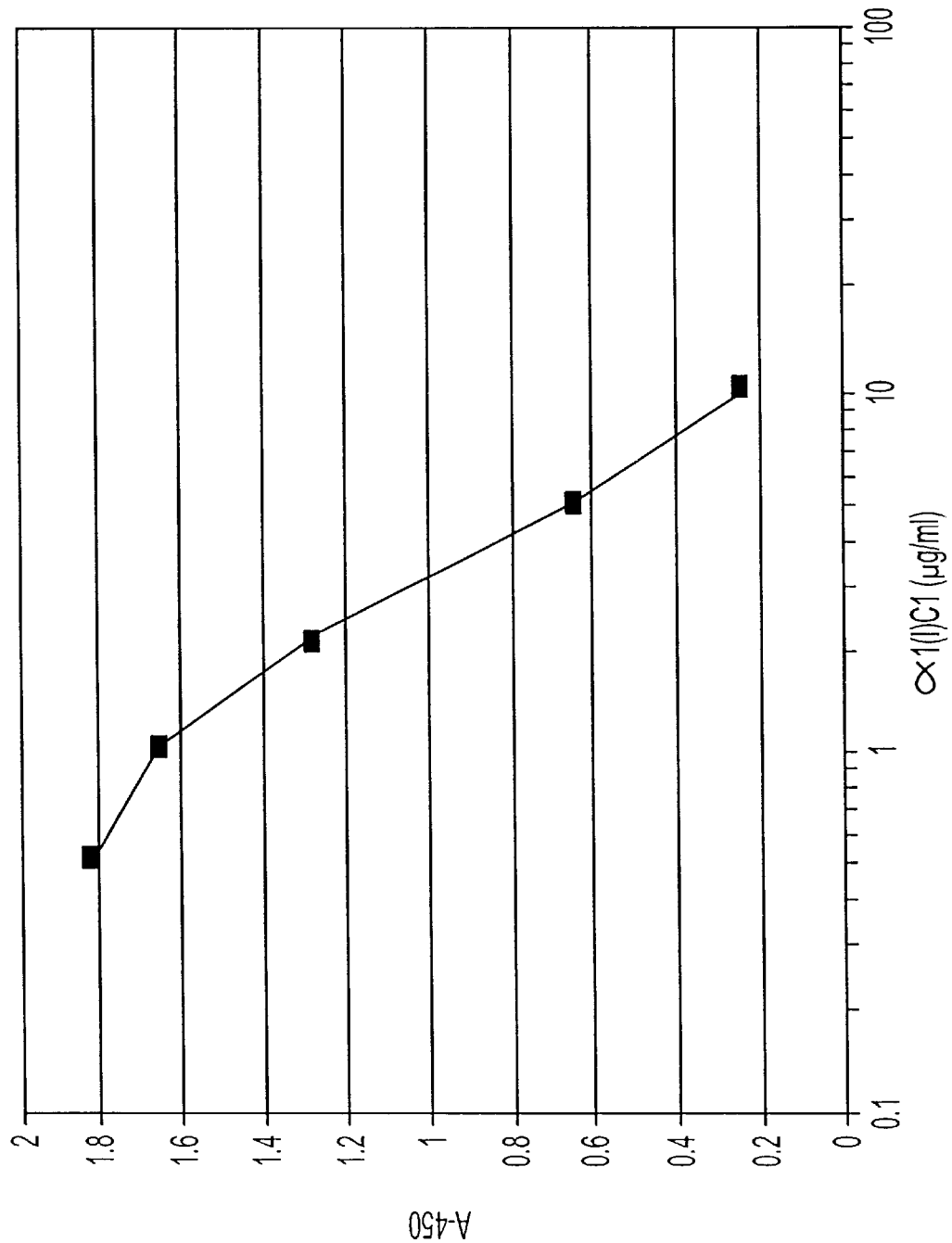
FIGS. 1, 2 and 3 are typical standard curves for the α1(I)C1 immunoassay (FIG. 1), the α1(I)N1 immunoassay (FIG. 2) and the α2(I)N1 immunoassay (FIG. 3) to be described in more detail in the examples.

In a preferred embodiment of the method according to the invention, the assaying of type I, II and III collagen fragments in urine is performed by an inhibition ELISA (enzyme linked immunosorbent assay) by metering off a sample of urine and contacting the sample with a synthetic peptide having a sequence derived from collagen and with an antibody, which is immunoreactive with the synthetic peptide. The synthetic peptide is immobilized on a solid support. The antibody is raised against the synthetic peptide.

The combined reagents and sample are incubated, and a peroxidase-conjugated (revealing) antibody is added. After another incubation, a peroxidase substrate solution is added. Following short final incubation, the enzyme reaction is stopped, and the absorbance is measured at 450 nm and compared with a standard curve obtained with standard solutions by the same procedure.

Synthetic peptides are used for the preparation of standards. The concentration of synthetic peptide in a stock solution of the relevant synthetic peptide is determined by quantitative amino acid determination. A two-fold dilution of the stock solution is prepared and subsequently used for the construction of the standard curve in the inhibition ELISA.

Preparation of Synthetic Peptides

The preparation of synthetic peptides may be performed according to procedures well known in the art, e.g. by solid-phase peptide synthesis techniques commonly described as "Merrifield synthesis". Also classical solution phase techniques may be used. Sequences of interest include potential sites for cross-linking (see for example Kühn, K., in *Immunochemistry of the Extracellular Matrix* 1:1–29 (1982), Eyre, D. R., *Ann. Rev. Biochem.* 53:717–48 (1984), or U.S. Pat. No. 5,140,103). Examples of such peptides sequences are given in table 1 below.

Regarding the synthetic peptides, it is possible to omit (or add) one or more amino acid residues from (or to) the crosslinkable site sequences without substantial loss of the ability to (a) raise antibodies recognizing the corresponding native collagen fragment or (b) inhibit the bindings of such antibodies to the native fragment. It is possible to use longer collagen fragments and/or chimeric peptides to raise the antibodies and, in principle, it is not necessary to use the same peptide as the immunogen and the competitor in the assay.

TABLE 1

Examples of Amino acid sequences with potential sites for cross-linking in various types of collagen to be used as a basis for synthetic peptides according to the present invention Collagen type I Potential sites
in telopeptides:   N                                              C

| α1 (I) N-term. | Asp-Glu-Lys-Ser-Thr-Gly-Gly (α1(I)N1) | SEQ. ID. NO. 1. |
| α1 (I) C-term. | Glu-Lys-Ala-His-Asp-Gly-Gly-Arg (α1(I)C1) | SEQ. ID. NO. 2. |
| α2 (I) N-term. | Gln-Tyr-Asp-Gly-Lys-Gly-Val-Gly (α2(I)N1) | SEQ. ID. NO. 3. |
| α2 (I) C-term. | no potential sites | |

Potential sites
in helix:

| α1 (I) (near N) | Gly-Met-Lys-Gly-His-Arg | SEQ. ID. NO. 4. |
| α1 (I) (near C) | Gly-Ile-Lys-Gly-His-Arg | SEQ. ID. NO. 5. |
| α2 (I) (near N) | Gly-Phe-Lys-Gly-Ile-Arg | SEQ. ID. NO. 6. |
| α2 (I) (near C) | Gly-Leu-Pro-Gly-Leu-Lys-Gly-His-Asn | SEQ. ID. NO. 7. |

Collagen type II

Potential sites
in telopeptides:   N                                              C

| α1 (II) N-term. | Pro-Gly-Pro-Lys-Gly-Glu | SEQ. ID. NO. 8. |
|                 | Gly-Gln-Lys-Gly-Glu-Pro | SEQ. ID. NO. 9. |

TABLE 1-continued

Examples of Amino acid sequences with potential sites
for cross-linking in various types of collagen to be used as a
basis for synthetic peptides according to the present invention

|   |   |   |
|---|---|---|
|   | Gly-Asp-Ile-Lys-Asp-Ile-Val | SEQ. ID. NO. 10. |
| α1 (II) C-term. | Glu-Lys-Gly-Pro-Asp | SEQ. ID. NO. 11. |
| Potential sites in helix: | | |
| α1 (II) (near N) | Gly-Val-Lys | SEQ. ID. NO. 12. |
|   | Pro-Gly-Val-Lys-Gly | SEQ. ID. NO. 13. |
| Collagen type III | | |
| Potential sites in telopeptides: | N                              C | |
| α1 (III) N-term. | Asp-Val-Lys-Ser-Gly-Val | SEQ. ID. NO. 14. |
| α1 (III) C-term. | Glu-Lys-Ala-Gly-Gly-Phe-Ala | SEQ. ID. NO. 15. |
| Potential sites in helix: | | |
| α1 (III) (near N) | Gly-Phe-Pro-Gly-Met-Lys-Gly-His-Arg | SEQ. ID. NO. 16. |
| α1 (III) (near C) | Gly-Ala-Ala-Gly-Ile-Lys-Gly-His-Arg | SEQ. ID. NO. 17. |

Preparation of antibodies

The methods for preparation of both monoclonal and polyclonal antibodies are well known in the art. For example, see Campbell, A. M., *Laboratory Techniques in Biochemistry and Molecular Biology*, Vol. 13 (1986). It is possible to produce antibodies to synthetic peptides by immunization. However, because of the relatively small molecular weight of these compounds it is preferred that the hapten be conjugated to a carrier molecule. Suitable carrier molecules include, but are not limited to, bovine serum albumin, thyroglobulin, ovalbumin, tetanus toxoid, and keyhole limpet hemocyanin. The preferred carrier is bovine serum albumin. To present the hapten in its most immunogenic form to the antibody producing cells of the immunized animal a number of alternative coupling protocols can be used. Suitable procedures include, but are not limited to, glutaraldehyde, carbodiimide, and periodate. Preferred binding agents are glutaraldehyde and carbodiimide.

The preparation of antibodies is carried out by conventional techniques including immunization with collagen fragments or synthetic peptides conjugated to a carrier. To improve the immunogenicity it is preferred that the immunogen be mixed with an adjuvant before injection. Examples of adjuvants include, but are not limited to, aluminum hydroxide, Freund's adjuvant, and immune-stimulating complexes (ISCOMs). ISCOMs can be made according to the method described by Morein, B. et al., *Nature* 308:457–460 (1984).

Either monoclonal or polyclonal antibodies to the hapten carrier molecule can be produced. For the production of monoclonal antibodies it is preferred that mice are immunized. Spleen cells from the immunized mouse are harvested, homogenized, and thereafter fused with cancer cells in the presence of polyethylene glycol to produce a cell hybrid which produces monoclonal antibodies specific for peptide fragments derived from collagen. Suitable cancer cells include, but are not limited to, myeloma, hepatoma, carcinoma, and sarcoma cells. Detailed descriptions of the production of monoclonal antibodies are provided in Goding, J. W., in *Monoclonal Antibodies: Principles and Practice*, (1986). A preferred preliminary screening protocol comprises the use of synthetic peptides conjugated to a carrier and coated onto the solid surface of a microtitre plate.

For the preparation of polyclonal antibodies, which are reactive with peptide fragments derived from collagen, different animal species can be immunized. Suitable species include, but are not limited to, chicken, rabbit and goat. Chicken and rabbit are preferred.

Antibody fragments are prepared by methods known in the art (see E. Ishikawa, *J. of Immunoassay* 3:209–327, 1983).

Conduct of Immunoassays

Accordingly, by utilization of an immunoassay with the antibodies prepared as above it is possible to assay a biological fluid sample without prior fractionation or hydrolysis. The specificity for the desired collagen in the biological fluid is supplied by the antibody in combination with the use of a synthetic peptide (against which the antibody was raised or in any event with which the antibody is immunochemically reactive) in the assay construction.

The immunoassays themselves are conducted using any procedure selected from the variety of standard assay protocols generally known in the art. As it is generally understood, the assay is constructed so as to rely on the interaction between the specific immunological binding partner and the desired analyte for specificity and to utilize some means to detect the complex formed by the analyte and the immunological binding partner. The immunological binding partner may be complexed to a solid support and used as a capture immunological binding partner for the analyte. This protocol may be run in a direct form, wherein the formation of analyte/immunological binding partner complex is detected, e.g. by a fluorescent, radioactive or enzymatic label, or it may be run in a competitive format wherein a labelled standard competes with the analyte for the immunological binding partner. The format may also be constructed as an agglutination assay or the complex may be precipitated by addition of a suitable precipitant to the reaction mixture. The specific design of the immunoassay protocol is open to a wide variety of choice, and the number of clinical assay devices and protocols available in the art is multitudinous. For a variety of such protocols, see U.S. Pat. No. 5,001,225.

The antibodies and revealing reagents for the conduct of an immunoassay using standard detection protocols, for example radioisotope labelling, fluorescent labelling or ELISA, either in a direct or competitive format, may conveniently be supplied as kits which include the necessary components and instructions for the assay. In one embodiment of the invention such a kit includes a microtiter plate coated with a relevant synthetic peptide, standard solutions for preparation of standard curve, a urine control for quality testing of the analytical run, rabbit antibodies reactive with the above-mentioned synthetic peptide, anti-rabbit immunoglobulins conjugated to peroxidase, a substrate solution, a stopping solution, a washing buffer and an instruction manual.

Since immunoassays can be constructed using antibodies and specific synthetic peptides, the ratios of the corresponding collagen fragment sequences in an appropriate biological fluid can be determined as well as their individual levels and their total. Thus, the assay can be designed to include antibodies which will result in determination of several native peptide sequences or determination of a single peptide sequence, or any desired combination thereof.

In addition to the use of the herein specified peptides as indicators of bone resorption, bone metabolic balance is advantageously determined by the substantially simultaneous determination of a marker of the formation of bone in the same or other appropriate biological fluid from the same individual. "Substantially simultaneous" means the same day, preferably within 4 hours. For example such markers include osteocalcin (also known as bone GLA protein of BGP), procollagen type I, bone alkaline phosphatase and total alkaline phosphatase. Suitable methods for the determination of these markers can be found, for example, in Delmas, P. D., et al., *J. Bone Min. Res.* 1:333–337 (1986).

The assay of the present invention which provides an index to determination of the metabolic status of tissues, which generate collagen-derived peptides when degradation occurs, are useful ^ in a variety of contexts. First, when considering the degradation of type I collagen, the assays are methods to assess an abnormal condition of a subject by indicating, for example, excessive bone resorption. This may show the presence of an osteoporotic condition or the metastatic progress of a malignancy. Other conditions characterized by excessive bone resorption include Paget's disease and hyperparathyroidism. Likewise, a number of other disease states involving connective tissue may be monitored by determination of the degradation of collagen. Examples are collagen type II degradation associated with rheumatoid arthritis and osteoarthritis and collagen type III degradation in vasculitis syndrome. Since the condition of the subject can be monitored continuously, application of these assays can also be used to monitor the progress of therapy administered to treat these or other conditions. Further, the assays can be used as a measure of toxicity, since the administration of toxic substances often results in tissue degradation.

Thus the assays may be applied in any situation wherein the metabolic condition of collagen tissues can be used as an index of the condition, treatment, or effect of substances directly administered to the subject or to which the subject is exposed in the environment.

The following examples are intended to illustrate, but not to limit the invention.

EXAMPLE 1

Immunoassays for Specific Peptide Sequences in Urine

Three peptides ($\alpha 1(I)C1$, $\alpha 1(I)N1$, and $\alpha 2(I)N1$) (see Table 1, p. 13) prepared by solid-phase techniques are used for the preparation of immunogens. For immunization, the peptides are covalently attached to bovine serum albumin using glutaraldehyde reagents and methods well known in the art. Both monoclonal and polyclonal antibodies are raised against the peptides. For production of monoclonal antibodies, Balb/c mice are immunized with peptide-BSA conjugates, and hybridoma cell lines are prepared using standard techniques after fusion of cells from the spleen or lymph nodes with Ag8 myeloma cells. Polyclonal antibodies are raised in rabbits and chicken. Screening of both antisera and hybridoma cell media were performed by ELISA using microtiter plates coated with the appropriate peptide-gelatin conjugate prepared using carbodiimide reagents and methods well known in the art.

Figure 2:
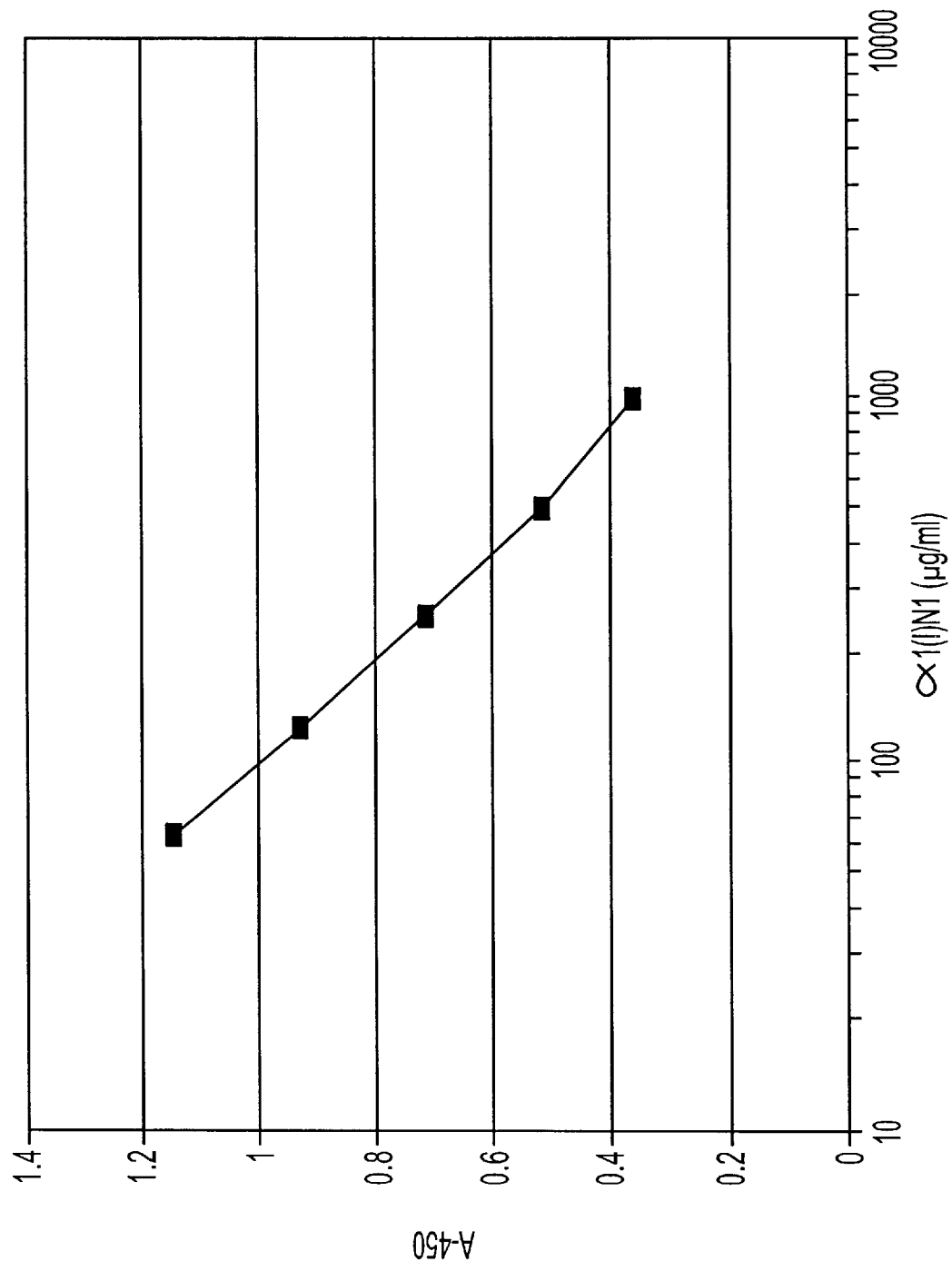
Figure 3:
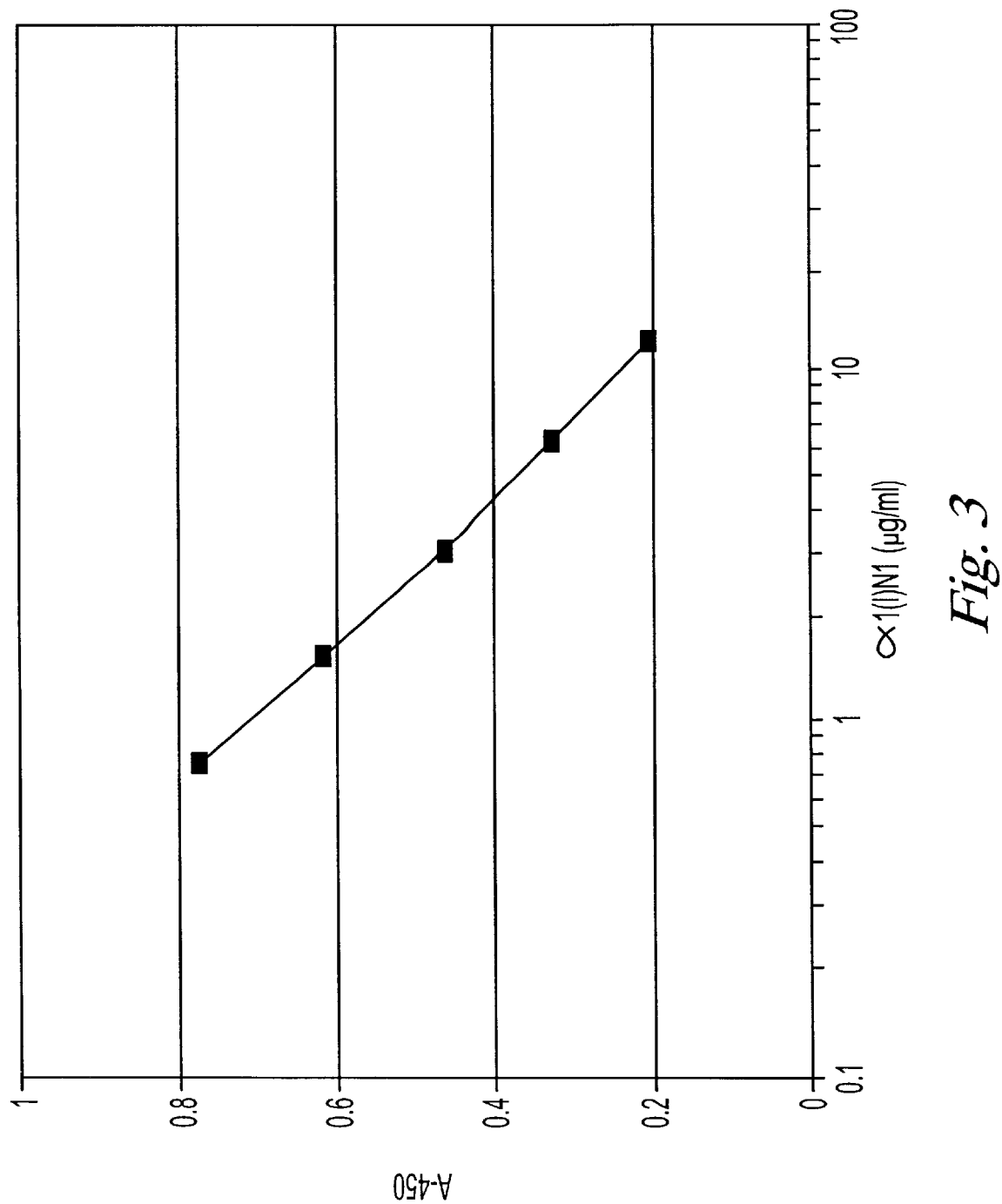

Assays for three of the peptide sequences ($\alpha 1(I)C1$, $\alpha 1(I)N1$, and $\alpha 2(I)N1$) in urine are performed by an inhibition ELISA as follows:

Urine samples (10 or 25 l) possibly containing collagen fragments or solutions containing 0.05–15 g peptide/ml as reference standards, respectively, are added to 75 l of immunological binding partners for the peptides diluted 1:5,000–1:20,000 in phosphate buffered saline containing 0.1% Tween-20 detergent (PBS-T) and including 0.1% (w/v) of BSA. Each sample is prepared in duplicate in flat-bottomed, 96-well microtiter plates previously coated with gelatine conjugate containing the appropriate peptide. After 60 minutes, the plates are washed with PBS-T (3 times) and the bound antibodies are detected by standard techniques with a horse radish peroxidase labelled antibody prepared against the species of the primary antibody. Peroxidase substrate is added and the color development is measured at 450 nm in an automated microtiter plate reader after stopping the enzyme reaction using 1 M H3PO4. Samples containing the analyte decrease the binding of primary antibody to the immunobilized peptide in the plate and thus have a reduced color concentration. The amount of analyte in the sample is quantified with reference to previously established curves from standards included on each plate computed using log-lin plots. FIGS. 1, 2 and 3 show typical standard curves for the $\alpha 1(I)C1$ immunoassay (FIG. 1), $\alpha 1(I)N1$ immunoassay (FIG. 2), and $\alpha 2(I)N1$ immunoassay (FIG. 3).

EXAMPLE 2

Correlation to Pyridinolin Determination on HPLC

On a number of unselected urine samples the concentration of total pyridinolin (HPLC method, see for example Uebelhart, D., *Bone and Mineral* 8:87–96 (1990)) was measured. Values obtained in this HPLC system were correlated to the values obtained in two immunoassays (α1(I) C1 peptide and α1(I)N1 peptide).

Figure 4:
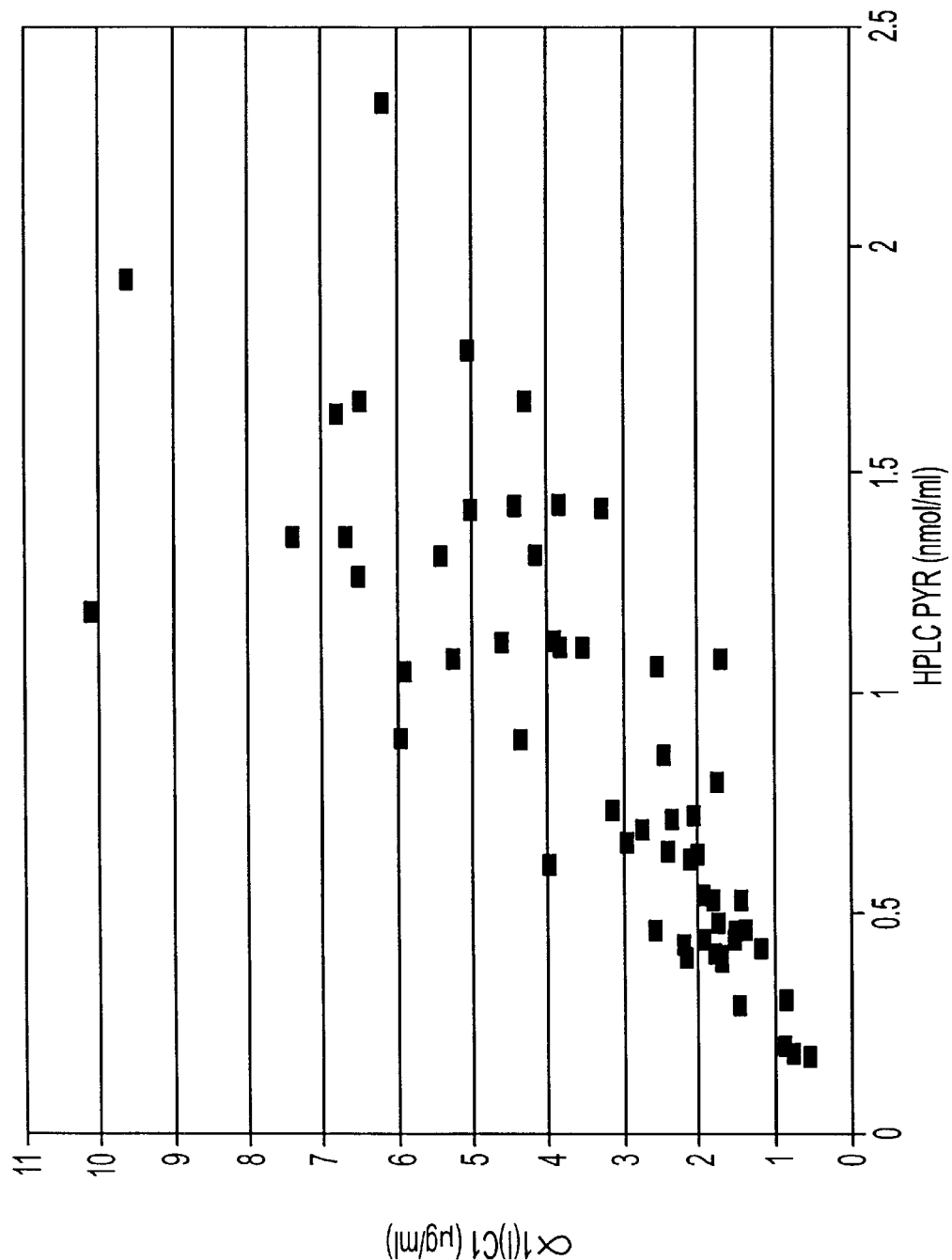
FIG. 4 shows the correlation between total pyridinolin (HPLC) and the α1(I)C1 immunoassay.

FIG. 4 shows the correlation between total pyridinolin (HPLC) and α1(I)C1 immunoassay (n=59). The correlation calculated by linear regression analysis is r=0.80.

Figure 5:
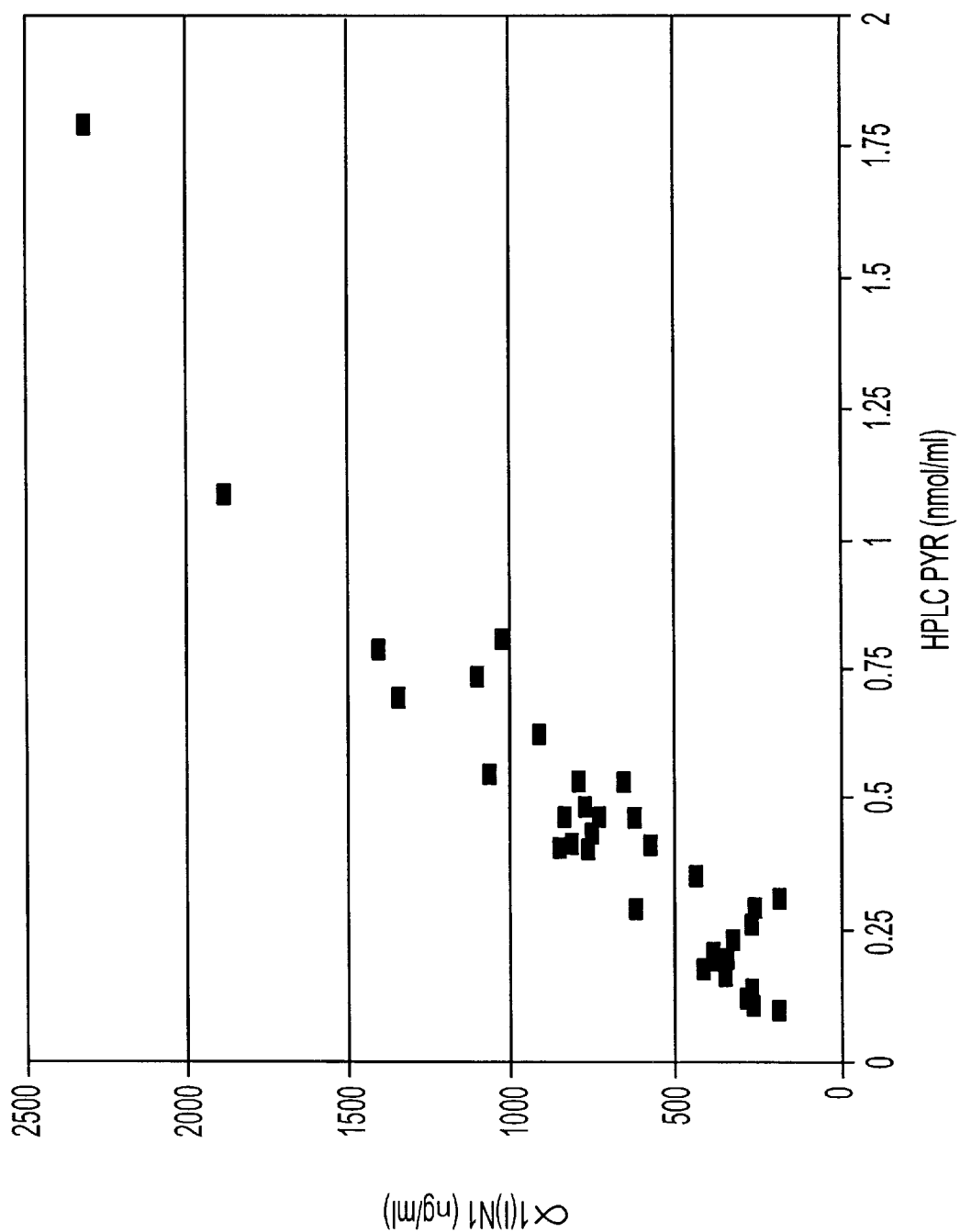
FIG. 5 shows the correlation between total pyridinolin (HPLC) and the α1(I)N1 immunoassay.

FIG. 5 shows the correlation between total pyridinolin (HPLC) and α1(I)N1 immunoassay (n=36). The correlation calculated by linear regression analysis is r=0.95.

EXAMPLE 3

Clinical Results

The immunoassay procedure (using the α1(I)C1 peptide) set forth in Example 1 was applied to urine samples from different individuals, and the amount of analyte was quantitated. The values obtained were related to the level of urinary creatinine in the urine sample as is commonly done for urine assays. The values obtained for normal, age-matched women (premenopausal and postmenopausal) are shown in Table 2.

TABLE 2

Measurement of α1(I)C1 peptide in urine samples from normal, age-matched women (premenopausal and postmenopausal)

| Group | α1(I)C1 peptide (g/mol creatinine) |
|---|---|
| Premenopausal (n = 104) | 0.263 ± 0.143 |
| Postmenopausal (n = 180) | 0.426 ± 0.190 |

Figure 6:
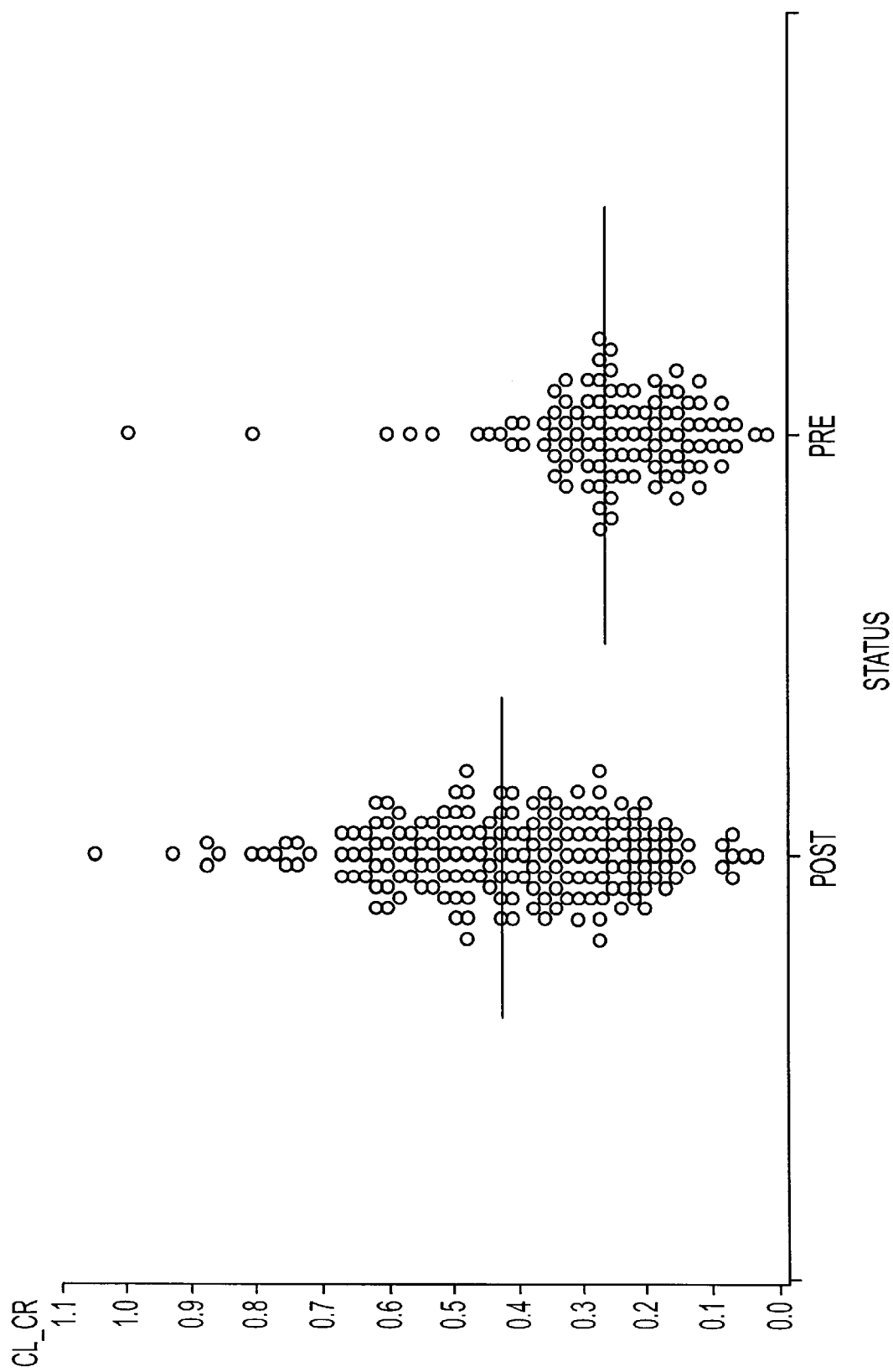
FIG. 6 shows the individual values of the measurement of α1(I)C1 peptide in urine samples from normal, age-matched women.

For individual values see FIG. 6.

The difference between the premenopausal and the postmenopausal values is highly significant (P<0.0001).

The z-score of a quantitative test procedure shows the ability of the procedure to distinguish between two populations. Table 3 below shows the z-score of the IC1 immunoassay and the state of the art measurement of pyridinolin on HPLC when applied to the same set of urine samples from normal, age-matched premenopausal (n=104) and postmenopausal women (n=180).

TABLE 3

Z-scores obtained for two different test procedures (total pyridinolin (HPLC) and α1(I)C1 immunoassay) when applied to urine samples from normal, age-matched women (premenopausal and postmenopausal)

| Test procedure | Z-score |
|---|---|
| α1(I)C1 immunoassay | 1.14 |
| Total pyridinolin (HPLC) | 1.25 |

As can be seen from Table 3, the abilities of the two methods to distinguish between patient populations are approximately alike.

For an assay to be used as an index of bone resorption it is very important to be able to measure the impact of a hormone replacement therapy (HRT). Table 4 shows the results from the α1(I)C1 immunoassay in such a study.

TABLE 4

Measurement of urine samples from women on a hormone replacement therapy and placebo in the α1(I)C1 immunoassay. Values given as percent of t = 0

| Group | α1(I)C1 peptide t = 0 | (µg/mol creatinine) t = 12 months |
|---|---|---|
| HRT (n = 92) | 0.457 ± 0.176 | 0.176 ± 0.103 |
| Placebo (n = 45) | 0.459 ± 0.209 | 0.402 ± 0.187 |

Figure 7:
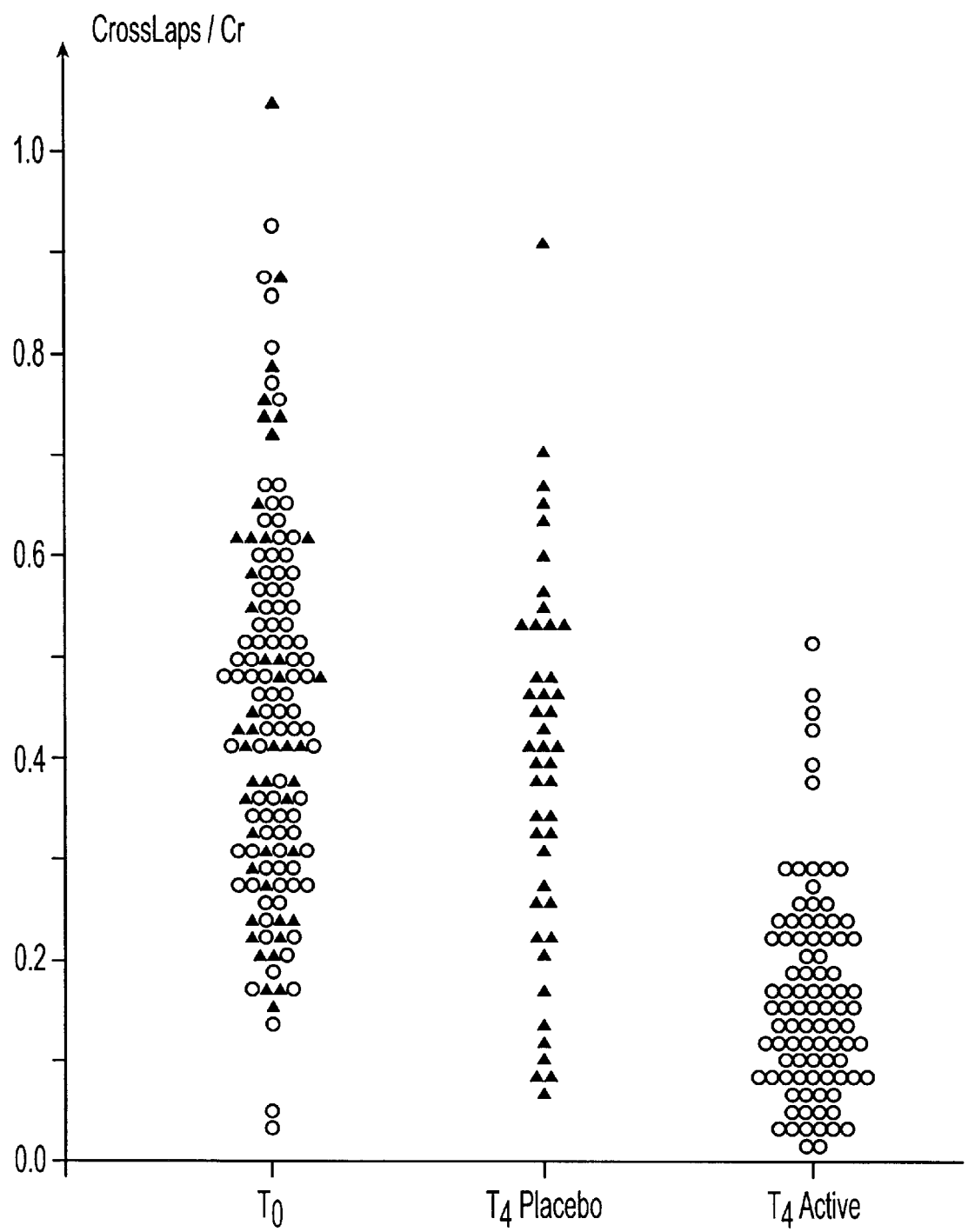
FIG. 7 shows the individual values of the measurement of urine samples from women on a hormone replacement therapy and placebo in the α1(I)C1 immunoassay.

For individual values see FIG. 7.

A highly significant drop in the group receiving HRT is seen after 12 months (P<0.001).

All cited patents, patent applications and literature are incorporated by reference in their entirety. In case of conflict, however, the present disclosure controls.

The invention has been described above by reference to specific embodiments. It will be apparent to those skilled in the art, however, that many additions, deletions and modifications are possible without departing from the spirit of the invention as claimed below.

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 7 amino acids
      (B) TYPE: amino acid
      (D) TOPOLOGY: linear (ii) MOLECULE TYPE: peptide (v) FRAGMENT TYPE: N-terminal (vi) ORIGINAL SOURCE:
      (A) ORGANISM: Homo sapiens (vii) IMMEDIATE SOURCE:
      (B) CLONE: COLLAGEN TYPE I-alpha 1 -N term

```
        (xi) SEQUENCE DESCRIPTION: SEQ ID NO:1:

Asp Glu Lys Ser Thr Gly Gly
1               5

(2) INFORMATION FOR SEQ ID NO:2:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (v) FRAGMENT TYPE: C-terminal (vi) ORIGINAL SOURCE:
          (A) ORGANISM: Homo sapiens (vii) IMMEDIATE SOURCE:
          (B) CLONE: COLLAGEN TYPE I -ALPHA 1- c TERMINAL (xi) SEQUENCE DESCRIPTION: SEQ ID NO:2:

Glu Lys Ala His Asp Gly Gly Arg
1               5

(2) INFORMATION FOR SEQ ID NO:3:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (v) FRAGMENT TYPE: N-terminal (vi) ORIGINAL SOURCE:
          (A) ORGANISM: Homo sapiens (vii) IMMEDIATE SOURCE:
          (B) CLONE: COLLAGEN TYPE I - ALPHA 2- N TERMINAL (xi) SEQUENCE DESCRIPTION: SEQ ID NO:3:

Gln Tyr Asp Gly Lys Gly Val Gly
1               5

(2) INFORMATION FOR SEQ ID NO:4:

(i) SEQUENCE CHARACTERISTICS:
          (A) LENGTH: 6 amino acids
          (B) TYPE: amino acid
          (D) TOPOLOGY: linear (ii) MOLECULE TYPE: peptide (v) FRAGMENT TYPE: internal (vi) ORIGINAL SOURCE:
          (A) ORGANISM: Homo sapiens (vii) IMMEDIATE SOURCE:
          (B) CLONE: COLLAGEN TYPE I -ALPHA 1- NEAR N (xi) SEQUENCE DESCRIPTION: SEQ ID NO:4:

Gly Met Lys Gly His Arg
1               5

(2) INFORMATION FOR SEQ ID NO:5:

(i) SEQUENCE CHARACTERISTICS:
          (A) LENGTH: 6 amino acids
```

```
            (B) TYPE: amino acid
            (D) TOPOLOGY: linear (ii) MOLECULE TYPE: peptide (v) FRAGMENT TYPE: C-terminal (vi) ORIGINAL SOURCE:
            (A) ORGANISM: Homo sapiens (vii) IMMEDIATE SOURCE:
            (B) CLONE: COLLAGEN TYPE I -ALPHA 1 NEAR c (xi) SEQUENCE DESCRIPTION: SEQ ID NO:5:

Gly Ile Lys Gly His Arg
1               5

(2) INFORMATION FOR SEQ ID NO:6:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Homo sapiens (vii) IMMEDIATE SOURCE:
            (B) CLONE: COLLAGEN TYPE I- ALPHA 2- NEAR N (xi) SEQUENCE DESCRIPTION: SEQ ID NO:6:

Gly Phe Lys Gly Ile Arg
1               5

(2) INFORMATION FOR SEQ ID NO:7:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Homo sapiens (vii) IMMEDIATE SOURCE:
            (B) CLONE: COLLAGEN TYPE I - ALPHA 2 - NEAR C (xi) SEQUENCE DESCRIPTION: SEQ ID NO:7:

Gly Leu Pro Gly Leu Lys Gly His Asn
1               5

(2) INFORMATION FOR SEQ ID NO:8:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: N-terminal (vi) ORIGINAL SOURCE:
            (A) ORGANISM: Homo sapiens
```

(vii) IMMEDIATE SOURCE:
            (B) CLONE: COLLAGEN TYPE II- ALPHA 1- N TERM (xi) SEQUENCE DESCRIPTION: SEQ ID NO:8:

Pro Gly Pro Lys Gly Glu
1               5

(2) INFORMATION FOR SEQ ID NO:9:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: N-terminal (vi) ORIGINAL SOURCE:
            (A) ORGANISM: Homo sapiens (vii) IMMEDIATE SOURCE:
            (B) CLONE: COLLAGEN TYPE II- ALPHA 1 N2

(xi) SEQUENCE DESCRIPTION: SEQ ID NO:9:

Gly Gln Lys Gly Glu Pro
1               5

(2) INFORMATION FOR SEQ ID NO:10:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: N-terminal (vi) ORIGINAL SOURCE:
            (A) ORGANISM: Homo sapiens (vii) IMMEDIATE SOURCE:
            (B) CLONE: COLLAGEN TYPE II - ALPHA 1- N3

(xi) SEQUENCE DESCRIPTION: SEQ ID NO:10:

Gly Asp Ile Lys Asp Ile Val
1               5

(2) INFORMATION FOR SEQ ID NO:11:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (v) FRAGMENT TYPE: C-terminal (vi) ORIGINAL SOURCE:
            (A) ORGANISM: Homo sapiens (vii) IMMEDIATE SOURCE:
            (B) CLONE: COLLAGEN TYPE II - ALPHA 1 -C TERM (xi) SEQUENCE DESCRIPTION: SEQ ID NO:11:

Glu Lys Gly Pro Asp
1               5

(2) INFORMATION FOR SEQ ID NO:12:

(i) SEQUENCE CHARACTERISTICS:
            (A) LENGTH: 3 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Homo sapiens (vii) IMMEDIATE SOURCE:
            (B) CLONE: COLLAGEN TYPE II - ALPHA 1 - NEAR N (xi) SEQUENCE DESCRIPTION: SEQ ID NO:12:

Gly Val Lys
1

(2) INFORMATION FOR SEQ ID NO:13:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Homo sapiens (vii) IMMEDIATE SOURCE:
            (B) CLONE: COLLAGEN TYPE II - ALPHA 1 -NEAR N2

(xi) SEQUENCE DESCRIPTION: SEQ ID NO:13:

Pro Gly Val Lys Gly
1               5

(2) INFORMATION FOR SEQ ID NO:14:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: N-terminal (vi) ORIGINAL SOURCE:
            (A) ORGANISM: Homo sapiens (vii) IMMEDIATE SOURCE:
            (B) CLONE: COLLAGEN TYPE III -ALPHA 1 - N TERM (xi) SEQUENCE DESCRIPTION: SEQ ID NO:14:

Asp Val Lys Ser Gly Val
1               5

(2) INFORMATION FOR SEQ ID NO:15:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: C-terminal

```
        (vi) ORIGINAL SOURCE:
             (A) ORGANISM: Homo sapiens (vii) IMMEDIATE SOURCE:
             (B) CLONE: COLLAGEN TYPE III - ALPHA 1 - C TERM (xi) SEQUENCE DESCRIPTION: SEQ ID NO:15:

Glu Lys Ala Gly Gly Phe Ala
1               5

(2) INFORMATION FOR SEQ ID NO:16:

(i) SEQUENCE CHARACTERISTICS:
             (A) LENGTH: 9 amino acids
             (B) TYPE: amino acid
             (D) TOPOLOGY: linear (ii) MOLECULE TYPE: peptide (v) FRAGMENT TYPE: internal (vi) ORIGINAL SOURCE:
             (A) ORGANISM: Homo sapiens (vii) IMMEDIATE SOURCE:
             (B) CLONE: COLLAGEN TYPE III - ALPHA 1 - NEAR N (xi) SEQUENCE DESCRIPTION: SEQ ID NO:16:

Gly Phe Pro Gly Met Lys Gly His Arg
1               5

(2) INFORMATION FOR SEQ ID NO:17:

(i) SEQUENCE CHARACTERISTICS:
             (A) LENGTH: 9 amino acids
             (B) TYPE: amino acid
             (D) TOPOLOGY: linear (ii) MOLECULE TYPE: peptide (v) FRAGMENT TYPE: internal (vi) ORIGINAL SOURCE:
             (A) ORGANISM: Homo sapiens (vii) IMMEDIATE SOURCE:
             (B) CLONE: COLLAGEN TYPE III - ALPHA 1 - NEAR C (xi) SEQUENCE DESCRIPTION: SEQ ID NO:17:

Gly Ala Ala Gly Ile Lys Gly His Arg
1               5

(2) INFORMATION FOR SEQ ID NO:18:

(i) SEQUENCE CHARACTERISTICS:
             (A) LENGTH: 1341 amino acids
             (B) TYPE: amino acid
             (D) TOPOLOGY: linear (ii) MOLECULE TYPE: protein (vi) ORIGINAL SOURCE:
             (A) ORGANISM: Homo sapiens (vii) IMMEDIATE SOURCE:
             (B) CLONE: COLLAGEN ALPHA 1 (I)

(xi) SEQUENCE DESCRIPTION: SEQ ID NO:18:

Met Phe Ser Phe Val Asp Leu Arg Leu Leu Leu Leu Leu Ala Ala Thr
1               5                  10                  15

Ala Leu Leu Thr His Gly Gln Glu Glu Gly Gln Val Glu Gly Gln Asp
```

-continued

```
                20                  25                  30
Glu Asp Ile Pro Pro Ile Thr Cys Val Gln Asn Gly Leu Arg Tyr His
            35                  40                  45

Asp Arg Asp Val Trp Lys Pro Glu Pro Cys Gln Ile Cys Val Cys Asp
 50                  55                  60

Asn Gly Lys Val Leu Cys Asp Val Ile Cys Asp Glu Thr Lys Asn
 65                  70                  75                  80

Cys Pro Gly Ala Glu Val Pro Glu Gly Glu Cys Cys Pro Val Cys Pro
                 85                  90                  95

Asp Gly Ser Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
130                 135                 140

Gly Pro Pro Gly Pro Pro Gly Pro Pro Gly Leu Gly Gly Asn Phe Ala
145                 150                 155                 160

Pro Gln Leu Tyr Gly Tyr Asp Glu Lys Ser Thr Gly Gly Ile Ser Val
                165                 170                 175

Pro Gly Pro Met Gly Pro Ser Gly Pro Arg Gly Leu Pro Gly Pro Pro
                180                 185                 190

Gly Ala Pro Gly Pro Glx Gly Phe Glx Gly Pro Pro Gly Glx Pro Gly
            195                 200                 205

Glx Pro Gly Ala Ser Gly Pro Met Gly Pro Arg Gly Pro Pro Gly Pro
    210                 215                 220

Pro Gly Lys Asx Gly Asx Asx Gly Glx Ala Gly Lys Pro Gly Arg Pro
225                 230                 235                 240

Gly Glx Arg Gly Pro Pro Gly Pro Glx Gly Ala Arg Gly Leu Pro Gly
                245                 250                 255

Thr Ala Gly Leu Pro Gly Met Lys Gly His Arg Gly Phe Ser Gly Leu
                260                 265                 270

Asx Gly Ala Lys Gly Asx Ala Gly Pro Ala Gly Pro Lys Gly Glx Pro
            275                 280                 285

Gly Ser Pro Gly Glx Asx Gly Ala Pro Gly Glx Met Gly Pro Pro Gly
290                 295                 300

Pro Lys Gly Asn Ser Gly Glu Pro Gly Ala Pro Gly Ser Lys Gly Asp
305                 310                 315                 320

Thr Gly Ala Lys Gly Glu Pro Gly Pro Val Gly Val Gln Gly Pro Pro
                325                 330                 335

Gly Pro Ala Gly Glu Glu Gly Lys Arg Gly Ala Arg Gly Glu Pro Gly
            340                 345                 350

Pro Thr Gly Leu Pro Gly Pro Pro Gly Glu Arg Gly Gly Pro Gly Ser
            355                 360                 365

Arg Gly Phe Pro Gly Ala Asp Gly Val Ala Gly Pro Lys Gly Pro Ala
            370                 375                 380

Gly Glu Arg Gly Ser Pro Gly Pro Ala Gly Pro Lys Gly Ser Pro Gly
385                 390                 395                 400

Glu Ala Gly Arg Pro Gly Glu Ala Gly Leu Pro Gly Ala Lys Gly Leu
                405                 410                 415

Thr Gly Ser Pro Gly Ser Pro Gly Pro Asp Gly Lys Thr Gly Pro Pro
                420                 425                 430

Gly Pro Ala Gly Gln Asp Gly Arg Pro Gly Pro Pro Gly Pro Pro Gly
            435                 440                 445
```

-continued

Ala Arg Gly Gln Ala Gly Val Met Gly Phe Pro Gly Pro Lys Gly Ala
    450                 455                 460
Ala Gly Glu Pro Gly Lys Ala Gly Glu Arg Gly Val Pro Gly Pro Pro
465                 470                 475                 480
Gly Ala Val Gly Pro Ala Gly Lys Asp Gly Glu Ala Gly Ala Gln Gly
                485                 490                 495
Pro Pro Gly Pro Ala Gly Pro Ala Gly Glu Arg Gly Glu Gln Gly Pro
            500                 505                 510
Ala Gly Ser Pro Gly Phe Gln Gly Leu Pro Gly Ala Gly Pro Pro
        515                 520                 525
Gly Glu Ala Gly Lys Pro Gly Glu Gln Gly Val Pro Gly Asp Leu Gly
    530                 535                 540
Ala Pro Gly Pro Ser Gly Ala Arg Gly Glu Arg Gly Phe Pro Gly Glu
545                 550                 555                 560
Arg Gly Val Gln Gly Pro Pro Gly Pro Ala Gly Pro Arg Gly Ala Asn
                565                 570                 575
Gly Ala Pro Gly Asn Asp Gly Ala Lys Gly Asp Ala Gly Ala Pro Gly
            580                 585                 590
Ala Pro Gly Ser Gln Gly Ala Pro Gly Leu Gln Gly Met Pro Gly Glu
        595                 600                 605
Arg Gly Ala Ala Gly Leu Pro Gly Pro Lys Gly Asp Arg Gly Asp Ala
    610                 615                 620
Gly Pro Lys Gly Ala Asp Gly Ser Pro Gly Lys Asp Gly Val Arg Gly
625                 630                 635                 640
Leu Thr Gly Pro Ile Gly Pro Pro Gly Pro Ala Gly Ala Pro Gly Asp
                645                 650                 655
Lys Gly Glu Ser Gly Pro Ser Gly Pro Ala Gly Pro Thr Gly Ala Arg
            660                 665                 670
Gly Ala Pro Gly Asp Arg Gly Glu Pro Gly Pro Pro Gly Pro Ala Gly
        675                 680                 685
Phe Ala Gly Pro Pro Gly Ala Asp Gly Gln Pro Gly Ala Lys Gly Glu
    690                 695                 700
Pro Gly Asp Ala Gly Ala Lys Gly Asp Ala Gly Pro Pro Gly Pro Ala
705                 710                 715                 720
Gly Pro Ala Gly Pro Pro Gly Pro Ile Gly Asn Val Gly Ala Pro Gly
                725                 730                 735
Ala Lys Gly Ala Arg Gly Ser Ala Gly Pro Pro Gly Ala Thr Gly Phe
            740                 745                 750
Pro Gly Ala Ala Gly Arg Val Gly Pro Pro Gly Pro Ser Gly Asn Ala
        755                 760                 765
Gly Pro Pro Gly Pro Pro Gly Pro Ala Gly Lys Glu Gly Gly Lys Gly
    770                 775                 780
Pro Arg Gly Glu Thr Gly Pro Ala Gly Arg Pro Gly Glu Val Gly Pro
785                 790                 795                 800
Pro Gly Pro Pro Gly Pro Ala Gly Glu Lys Gly Ser Pro Gly Ala Asp
                805                 810                 815
Gly Pro Ala Gly Ala Pro Gly Thr Pro Gly Pro Gln Gly Ile Ala Gly
            820                 825                 830
Gln Arg Gly Val Val Gly Leu Pro Gly Gln Arg Gly Glu Arg Gly Phe
        835                 840                 845
Pro Gly Leu Pro Gly Pro Ser Gly Glu Pro Gly Lys Gln Gly Pro Ser
    850                 855                 860

```
Gly Ala Ser Gly Glu Arg Gly Pro Pro Gly Pro Met Gly Pro Pro Gly
865                 870                 875                 880

Leu Ala Gly Pro Pro Gly Glu Ser Gly Arg Glu Gly Ala Pro Gly Ala
            885                 890                 895

Glu Gly Ser Pro Gly Arg Asp Gly Ser Pro Gly Ala Lys Gly Asp Arg
        900                 905                 910

Gly Glu Thr Gly Pro Ala Gly Pro Pro Gly Ala Xaa Gly Ala Xaa Gly
            915                 920                 925

Ala Pro Gly Pro Val Gly Pro Ala Gly Lys Ser Gly Asp Arg Gly Glu
930                 935                 940

Thr Gly Pro Ala Gly Pro Ala Gly Pro Val Gly Pro Ala Gly Ala Arg
945                 950                 955                 960

Gly Pro Ala Gly Pro Gln Gly Pro Arg Gly Asp Lys Gly Glu Thr Gly
            965                 970                 975

Glu Gln Gly Asp Arg Gly Ile Lys Gly His Arg Gly Phe Ser Gly Leu
        980                 985                 990

Gln Gly Pro Pro Gly Pro Pro Gly Ser Pro Gly Glu Gln Gly Pro Ser
            995                 1000                1005

Gly Ala Ser Gly Pro Ala Gly Pro Arg Gly Pro Pro Gly Ser Ala Gly
        1010                1015                1020

Ala Pro Gly Lys Asp Gly Leu Asn Gly Leu Pro Gly Pro Ile Gly Pro
1025                1030                1035                1040

Pro Gly Pro Arg Gly Arg Thr Gly Asp Ala Gly Pro Val Gly Pro Pro
            1045                1050                1055

Gly Pro Pro Gly Pro Pro Gly Pro Pro Gly Pro Pro Ser Ala Gly Phe
            1060                1065                1070

Asp Phe Ser Phe Leu Pro Gln Pro Pro Gln Glu Lys Ala His Lys Gly
            1075                1080                1085

Gly Arg Tyr Tyr Arg Ala Asp Asp Ala Asn Val Val Arg Asp Arg Asp
        1090                1095                1100

Leu Glu Val Asp Thr Thr Leu Lys Ser Leu Ser Gln Gln Ile Glu Asn
1105                1110                1115                1120

Ile Arg Ser Pro Glu Gly Xaa Arg Lys Asn Pro Ala Arg Thr Cys Arg
            1125                1130                1135

Asp Leu Lys Met Cys His Ser Asp Trp Lys Ser Gly Glu Tyr Trp Ile
            1140                1145                1150

Asp Pro Asn Gln Gly Cys Asn Leu Asp Ala Ile Lys Val Phe Cys Asn
            1155                1160                1165

Met Glu Thr Gly Glu Thr Cys Val Tyr Pro Thr Gln Pro Ser Val Ala
            1170                1175                1180

Gln Lys Asn Trp Tyr Ile Ser Lys Asn Pro Lys Asp Lys Asp Arg His
1185                1190                1195                1200

Val Trp Phe Gly Glu Ser Met Thr Asp Gly Phe Gln Phe Glu Tyr Gly
            1205                1210                1215

Gly Gln Gly Ser Asp Pro Ala Asp Val Ala Ile Gln Leu Thr Phe Leu
            1220                1225                1230

Arg Leu Met Ser Thr Glu Ala Ser Gln Asn Ile Thr Tyr His Cys Lys
            1235                1240                1245

Asn Ser Val Ala Tyr Met Asp Gln Gln Thr Gly Asn Leu Lys Lys Ala
            1250                1255                1260

Leu Leu Leu Xaa Gly Ser Asn Glu Ile Glu Ile Arg Ala Glu Gly Asn
1265                1270                1275                1280

Ser Arg Phe Thr Tyr Ser Val Thr Val Asp Gly Cys Thr Ser His Thr
```

```
                        1285              1290              1295
Gly Ala Trp Gly Lys Thr Val Ile Glu Tyr Lys Thr Thr Lys Ser Ser
            1300              1305              1310

Arg Leu Pro Ile Ile Asp Val Ala Pro Leu Asp Val Gly Ala Pro Asp
            1315              1320              1325

Gln Glu Phe Gly Phe Asp Val Gly Pro Val Cys Phe Leu
            1330              1335              1340

(2) INFORMATION FOR SEQ ID NO:19:

(i) SEQUENCE CHARACTERISTICS:
         (A) LENGTH: 1366 amino acids
         (B) TYPE: amino acid
         (D) TOPOLOGY: linear (ii) MOLECULE TYPE: protein (vi) ORIGINAL SOURCE:
         (A) ORGANISM: Homo sapiens (vii) IMMEDIATE SOURCE:
         (B) CLONE: collagen alpha 2- type I (xi) SEQUENCE DESCRIPTION: SEQ ID NO:19:

Met Leu Ser Phe Val Asp Thr Arg Thr Leu Leu Leu Leu Ala Val Thr
1               5                  10                  15

Leu Cys Leu Ala Thr Cys Gln Ser Leu Gln Glu Glu Thr Val Arg Lys
            20                  25                  30

Gly Pro Ala Gly Asp Arg Gly Pro Arg Gly Glu Arg Gly Pro Pro Gly
        35                  40                  45

Pro Pro Gly Arg Asp Gly Glu Asp Gly Pro Thr Gly Pro Pro Gly Pro
    50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
            100                 105                 110

Phe Gln Gly Pro Ala Gly Glu Pro Gly Glu Pro Gly Gln Thr Gly Pro
        115                 120                 125

Ala Gly Ala Arg Gly Pro Ala Gly Pro Pro Gly Lys Ala Gly Glu Asp
    130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175

Lys Gly Ile Arg Gly His Asn Gly Leu Asp Gly Leu Lys Gly Gln Pro
            180                 185                 190

Gly Ala Pro Gly Val Lys Gly Glu Pro Gly Ala Pro Gly Glu Asn Gly
        195                 200                 205

Thr Pro Gly Gln Thr Gly Ala Arg Gly Leu Pro Gly Glu Arg Gly Arg
    210                 215                 220

Val Gly Ala Pro Gly Pro Ala Gly Ala Arg Gly Ser Asp Gly Ser Val
225                 230                 235                 240

Gly Pro Val Gly Pro Ala Gly Pro Asn Gly Ser Ala Gly Pro Pro Gly
                245                 250                 255

Phe Pro Gly Ala Pro Gly Pro Lys Gly Glu Ile Gly Ala Val Gly Asn
            260                 265                 270
```

-continued

```
Ala Gly Pro Thr Gly Pro Ala Gly Pro Arg Gly Glu Val Gly Leu Pro
            275                 280                 285
Gly Leu Ser Gly Pro Val Gly Pro Pro Gly Asn Pro Gly Ala Asn Gly
        290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Pro Gly Ala Ala
                325                 330                 335
Gly Thr Thr Gly Ala Arg Gly Leu Val Gly Glu Pro Gly Pro Ala Gly
            340                 345                 350
Ser Lys Gly Glu Ser Gly Asn Lys Gly Glu Pro Gly Ser Ala Gly Pro
        355                 360                 365
Gln Gly Pro Pro Gly Pro Ser Gly Glu Glu Lys Arg Gly Pro Asn
    370                 375                 380
Gly Glu Ala Gly Ser Ala Gly Pro Pro Gly Pro Gly Leu Arg Gly
385                 390                 395                 400
Ser Pro Gly Ser Arg Gly Leu Pro Gly Ala Asp Gly Arg Ala Gly Val
                405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
        435                 440                 445
Pro Arg Gly Leu Pro Gly Ser Pro Gly Asn Ile Gly Pro Ala Gly Lys
    450                 455                 460
Glu Gly Pro Val Gly Leu Pro Gly Ile Asp Gly Arg Pro Gly Pro Ile
465                 470                 475                 480
Gly Pro Val Gly Ala Arg Gly Glu Pro Gly Asn Ile Gly Phe Pro Gly
                485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
        515                 520                 525
Gly Ala Gln Gly Pro Pro Gly Pro Gln Gly Val Gln Gly Gly Lys Gly
    530                 535                 540
Glu Gln Gly Pro Ala Gly Pro Pro Gly Phe Gln Gly Leu Pro Gly Pro
545                 550                 555                 560
Ser Gly Pro Ala Gly Glu Val Gly Lys Pro Gly Glu Arg Gly Leu His
                565                 570                 575
Gly Glu Phe Gly Leu Pro Gly Pro Ala Gly Pro Arg Gly Glu Arg Gly
            580                 585                 590
Pro Pro Gly Glu Ser Gly Ala Ala Gly Pro Thr Gly Pro Ile Gly Ser
        595                 600                 605
Arg Gly Pro Ser Gly Pro Pro Gly Pro Asp Gly Asn Lys Gly Glu Pro
    610                 615                 620
Gly Val Val Gly Ala Val Gly Thr Ala Gly Pro Ser Gly Pro Ser Gly
625                 630                 635                 640
Leu Pro Gly Glu Arg Gly Ala Ala Gly Ile Pro Gly Gly Lys Gly Glu
                645                 650                 655
Lys Gly Glu Pro Gly Leu Arg Gly Glu Ile Gly Asn Pro Gly Arg Asp
            660                 665                 670
Gly Ala Arg Gly Ala His Gly Ala Val Gly Ala Pro Gly Pro Ala Gly
        675                 680                 685
```

-continued

```
Ala Thr Gly Asp Arg Gly Glu Ala Gly Ala Gly Pro Ala Gly Pro
    690                 695                 700
Ala Gly Pro Arg Gly Ser Pro Gly Glu Arg Gly Glu Val Gly Pro Ala
705                 710                 715                 720
Gly Pro Asn Gly Phe Ala Gly Pro Ala Gly Ala Ala Gly Gln Pro Gly
            725                 730                 735
Ala Lys Gly Glu Arg Gly Gly Lys Gly Pro Lys Gly Glu Asn Gly Val
            740                 745                 750
Val Gly Pro Thr Gly Pro Val Gly Ala Ala Gly Pro Ala Gly Pro Asn
            755                 760                 765
Gly Pro Pro Gly Pro Ala Gly Ser Arg Gly Asp Gly Gly Pro Pro Gly
            770                 775                 780
Met Thr Gly Phe Pro Gly Ala Ala Gly Arg Thr Gly Pro Pro Gly Pro
785                 790                 795                 800
Ser Gly Ile Ser Gly Pro Pro Gly Pro Pro Gly Pro Ala Gly Lys Glu
            805                 810                 815
Gly Leu Arg Gly Pro Arg Gly Asp Gln Gly Pro Val Gly Arg Thr Gly
            820                 825                 830
Glu Val Gly Ala Val Gly Pro Pro Gly Phe Ala Gly Glu Lys Gly Pro
            835                 840                 845
Ser Gly Glu Ala Gly Thr Ala Gly Pro Pro Gly Thr Pro Gly Pro Gln
            850                 855                 860
Gly Leu Leu Gly Ala Pro Gly Ile Leu Gly Leu Pro Gly Ser Arg Gly
865                 870                 875                 880
Glu Arg Gly Leu Pro Gly Val Ala Gly Ala Val Gly Glu Pro Gly Pro
            885                 890                 895
Leu Gly Ile Ala Gly Pro Pro Gly Ala Arg Gly Pro Pro Gly Ala Val
            900                 905                 910
Gly Ser Pro Gly Val Asn Gly Ala Pro Gly Glu Ala Gly Arg Asp Gly
            915                 920                 925
Asn Pro Gly Asn Asp Gly Pro Pro Gly Arg Asp Gly Gln Pro Gly His
            930                 935                 940
Lys Gly Glu Arg Gly Tyr Pro Gly Asn Ile Gly Pro Val Gly Ala Ala
945                 950                 955                 960
Gly Ala Pro Gly Pro His Gly Pro Val Gly Pro Ala Gly Lys His Gly
            965                 970                 975
Asn Arg Gly Glu Thr Gly Pro Ser Gly Pro Val Gly Pro Ala Gly Ala
            980                 985                 990
Val Gly Pro Arg Gly Pro Ser Gly Pro Gln Gly Ile Arg Gly Asp Lys
            995                 1000                1005
Gly Glu Pro Gly Glu Lys Gly Pro Arg Gly Leu Pro Gly Phe Lys Gly
            1010                1015                1020
His Asn Gly Leu Gln Gly Leu Pro Gly Ile Ala Gly His His Gly Asp
1025                1030                1035                1040
Gln Gly Ala Pro Gly Ser Val Gly Pro Ala Gly Pro Arg Gly Pro Ala
            1045                1050                1055
Gly Pro Ser Gly Pro Ala Gly Lys Asp Gly Arg Thr Gly His Pro Gly
            1060                1065                1070
Thr Val Gly Pro Ala Gly Ile Arg Gly Pro Gln Gly His Gln Gly Pro
            1075                1080                1085
Ala Gly Pro Pro Gly Pro Pro Gly Pro Pro Gly Pro Pro Gly Val Ser
            1090                1095                1100
Gly Gly Gly Tyr Asp Phe Gly Tyr Asp Gly Asp Phe Tyr Arg Ala Asp
```

-continued

```
                1105                1110                1115                1120

Gln Pro Arg Ser Ala Pro Ser Leu Arg Pro Lys Asp Tyr Glu Val Asp
                        1125                1130                1135

Ala Thr Leu Lys Ser Leu Asn Asn Gln Ile Glu Thr Leu Leu Thr Pro
                        1140                1145                1150

Glu Gly Ser Arg Lys Asn Pro Ala Arg Thr Cys Arg Asp Leu Arg Leu
                        1155                1160                1165

Ser His Pro Glu Trp Ser Ser Gly Tyr Tyr Trp Ile Asp Pro Asn Gln
                        1170                1175                1180

Gly Cys Thr Met Glu Ala Ile Lys Val Tyr Cys Asp Phe Pro Thr Gly
        1185                1190                1195                1200

Glu Thr Cys Ile Arg Ala Gln Pro Glu Asn Ile Pro Ala Lys Asn Trp
                        1205                1210                1215

Tyr Arg Ser Ser Lys Asp Lys Lys His Val Trp Leu Gly Glu Thr Ile
                        1220                1225                1230

Asn Ala Gly Ser Gln Phe Glu Tyr Asn Val Glu Gly Val Thr Ser Lys
                        1235                1240                1245

Glu Met Ala Thr Gln Leu Ala Phe Met Arg Leu Leu Ala Asn Tyr Ala
                        1250                1255                1260

Ser Gln Asn Ile Thr Tyr His Cys Lys Asn Ser Ile Ala Tyr Met Asp
        1265                1270                1275                1280

Glu Glu Thr Gly Asn Leu Lys Lys Ala Val Ile Leu Gln Gly Ser Asn
                        1285                1290                1295

Asp Val Glu Leu Val Ala Glu Gly Asn Ser Arg Phe Thr Tyr Thr Val
                        1300                1305                1310

Leu Val Asp Gly Cys Ser Lys Lys Thr Asn Glu Trp Gly Lys Thr Ile
                        1315                1320                1325

Ile Glu Tyr Lys Thr Asn Lys Pro Ser Arg Leu Pro Phe Leu Asp Ile
                        1330                1335                1340

Ala Pro Leu Asp Ile Gly Gly Ala Asp His Glu Phe Phe Val Asp Ile
        1345                1350                1355                1360

Gly Pro Val Cys Phe Lys
                        1365

(2) INFORMATION FOR SEQ ID NO:20:

(i) SEQUENCE CHARACTERISTICS:
        (A) LENGTH: 1418 amino acids
        (B) TYPE: amino acid
        (D) TOPOLOGY: linear (ii) MOLECULE TYPE: protein (vi) ORIGINAL SOURCE:
        (A) ORGANISM: Homo sapiens (vii) IMMEDIATE SOURCE:
        (B) CLONE: COLLAGEN -ALPHA 1 (II)

(xi) SEQUENCE DESCRIPTION: SEQ ID NO:20:

Met Ile Arg Leu Gly Ala Pro Gln Ser Leu Val Leu Leu Thr Leu Leu
1               5                   10                  15

Val Ala Ala Val Leu Arg Cys Gln Gly Gln Asp Val Arg Gln Pro Gly
                20                  25                  30

Pro Lys Gly Gln Lys Gly Glu Pro Gly Asp Ile Lys Asp Ile Val Gly
                35                  40                  45

Pro Lys Gly Pro Pro Gly Pro Gln Gly Pro Ala Gly Glu Gln Gly Pro
        50                  55                  60
```

-continued

```
Arg Gly Asp Arg Gly Asp Lys Gly Glu Lys Gly Ala Pro Gly Pro Arg
 65                  70                  75                  80

Gly Arg Asp Gly Glu Pro Gly Thr Leu Gly Asn Pro Gly Pro Pro Gly
                 85                  90                  95

Pro Pro Gly Pro Gly Pro Pro Gly Leu Gly Gly Asn Phe Ala Ala
            100                 105                 110

Gln Met Ala Gly Gly Phe Asp Glu Lys Ala Gly Gly Ala Gln Leu Gly
            115                 120                 125

Val Met Gln Gly Pro Met Gly Pro Met Gly Pro Arg Gly Pro Pro Gly
        130                 135                 140

Pro Ala Gly Ala Pro Gly Pro Gln Gly Phe Gln Gly Asn Pro Gly Glu
145                 150                 155                 160

Pro Gly Glu Pro Gly Val Ser Gly Pro Met Gly Pro Arg Gly Pro Pro
                165                 170                 175

Gly Pro Pro Gly Lys Pro Gly Asp Asp Gly Glu Ala Gly Lys Pro Gly
                180                 185                 190

Lys Ala Gly Glu Arg Gly Pro Pro Gly Pro Gln Gly Ala Arg Gly Phe
            195                 200                 205

Pro Gly Thr Pro Gly Leu Pro Gly Val Lys Gly His Arg Gly Tyr Pro
            210                 215                 220

Gly Leu Asp Gly Ala Lys Gly Glu Ala Gly Ala Pro Gly Val Lys Gly
225                 230                 235                 240

Glu Ser Gly Ser Pro Gly Glu Asn Gly Ser Pro Gly Pro Met Gly Pro
                245                 250                 255

Arg Gly Leu Pro Gly Glu Arg Gly Arg Thr Gly Pro Ala Gly Ala Ala
            260                 265                 270

Gly Ala Arg Gly Asn Asp Gly Gln Pro Gly Pro Ala Gly Pro Pro Gly
            275                 280                 285

Pro Val Gly Pro Ala Gly Gly Pro Gly Phe Pro Gly Ala Pro Gly Ala
        290                 295                 300

Lys Gly Glu Ala Gly Pro Thr Gly Ala Arg Gly Pro Glu Gly Ala Gln
305                 310                 315                 320

Gly Pro Arg Gly Glu Pro Gly Thr Pro Gly Ser Pro Gly Pro Ala Gly
                325                 330                 335

Ala Ser Gly Asn Pro Gly Thr Asp Gly Ile Pro Gly Ala Lys Gly Ser
            340                 345                 350

Ala Gly Ala Pro Gly Ile Ala Gly Ala Pro Gly Phe Pro Gly Pro Arg
            355                 360                 365

Gly Pro Pro Asp Pro Gln Gly Ala Thr Gly Pro Leu Gly Pro Lys Gly
            370                 375                 380

Gln Thr Gly Lys Pro Gly Ile Ala Gly Phe Lys Gly Glu Gln Gly Pro
385                 390                 395                 400

Lys Gly Glu Pro Gly Pro Ala Gly Pro Gln Gly Ala Pro Gly Pro Ala
                405                 410                 415

Gly Glu Glu Gly Lys Arg Gly Ala Arg Gly Glu Pro Gly Gly Val Gly
            420                 425                 430

Pro Ile Gly Pro Pro Gly Glu Arg Gly Ala Pro Gly Asn Arg Gly Phe
        435                 440                 445

Pro Gly Gln Asp Gly Leu Ala Gly Pro Lys Gly Ala Pro Gly Glu Arg
        450                 455                 460

Gly Pro Ser Gly Leu Ala Gly Pro Lys Gly Ala Asn Gly Asp Pro Gly
465                 470                 475                 480
```

-continued

```
Arg Pro Gly Glu Pro Gly Leu Pro Gly Ala Arg Gly Leu Thr Gly Arg
            485                 490                 495
Pro Gly Asp Ala Gly Pro Gln Gly Lys Val Gly Pro Ser Gly Ala Pro
            500                 505                 510
Gly Glu Asp Gly Arg Pro Gly Pro Pro Gly Pro Gln Gly Ala Arg Gly
            515                 520                 525
Gln Pro Gly Val Met Gly Phe Pro Gly Pro Lys Gly Ala Asn Gly Glu
            530                 535                 540
Pro Gly Lys Ala Gly Glu Lys Gly Leu Pro Gly Ala Pro Gly Leu Arg
545                 550                 555                 560
Gly Leu Pro Gly Lys Asp Gly Glu Thr Gly Ala Glu Gly Pro Pro Gly
                565                 570                 575
Pro Ala Gly Pro Ala Gly Glu Arg Gly Glu Gln Gly Ala Pro Gly Pro
            580                 585                 590
Ser Gly Phe Gln Gly Leu Pro Gly Pro Pro Gly Pro Pro Gly Glu Gly
            595                 600                 605
Gly Lys Pro Gly Asp Gln Gly Val Pro Gly Glu Ala Gly Ala Pro Gly
            610                 615                 620
Leu Val Gly Pro Arg Gly Glu Arg Gly Phe Pro Gly Glu Arg Gly Ser
625                 630                 635                 640
Pro Gly Ala Gln Gly Leu Gln Gly Pro Arg Gly Leu Pro Gly Thr Pro
                645                 650                 655
Gly Thr Asp Gly Pro Lys Gly Ala Ser Gly Pro Ala Gly Pro Pro Gly
            660                 665                 670
Ala Gln Gly Pro Pro Gly Leu Gln Gly Met Pro Gly Glu Arg Gly Ala
            675                 680                 685
Ala Gly Ile Ala Gly Pro Lys Gly Asp Arg Gly Asp Val Gly Glu Lys
            690                 695                 700
Gly Pro Glu Gly Ala Pro Gly Lys Asp Gly Gly Arg Gly Leu Thr Gly
705                 710                 715                 720
Pro Ile Gly Pro Pro Gly Pro Ala Gly Ala Asn Gly Glu Lys Gly Glu
                725                 730                 735
Val Gly Pro Pro Gly Pro Ala Gly Ser Ala Gly Ala Arg Gly Ala Pro
            740                 745                 750
Gly Glu Arg Gly Glu Thr Gly Pro Pro Gly Thr Ser Gly Ile Ala Gly
            755                 760                 765
Pro Pro Gly Ala Asp Gly Gln Pro Gly Ala Lys Gly Glu Gln Gly Glu
            770                 775                 780
Ala Gly Gln Lys Gly Asp Ala Gly Ala Pro Gly Pro Gln Gly Pro Ser
785                 790                 795                 800
Gly Ala Pro Gly Pro Gln Gly Pro Thr Gly Val Thr Gly Pro Lys Gly
                805                 810                 815
Ala Arg Gly Ala Gln Gly Pro Pro Gly Ala Thr Gly Phe Pro Gly Ala
            820                 825                 830
Ala Gly Arg Val Gly Pro Pro Gly Ser Asn Gly Asn Pro Gly Pro Pro
            835                 840                 845
Gly Pro Pro Gly Pro Ser Gly Lys Asp Gly Pro Lys Gly Ala Arg Gly
            850                 855                 860
Asp Ser Gly Pro Pro Gly Arg Ala Gly Glu Pro Gly Leu Gln Gly Pro
865                 870                 875                 880
Ala Gly Pro Pro Gly Glu Lys Gly Glu Pro Gly Asp Asp Gly Pro Ser
                885                 890                 895
Gly Ala Glu Gly Pro Pro Gly Pro Gln Gly Leu Ala Gly Gln Arg Gly
```

-continued

```
                    900                 905                 910
Ile Val Gly Leu Pro Gly Gln Arg Gly Glu Arg Gly Phe Pro Gly Leu
                915                 920                 925

Pro Gly Pro Ser Gly Glu Pro Gly Gln Gln Gly Ala Pro Gly Ala Ser
            930                 935                 940

Gly Asp Arg Gly Pro Pro Gly Pro Val Gly Pro Pro Gly Leu Thr Gly
945                 950                 955                 960

Pro Ala Gly Glu Pro Gly Arg Glu Gly Ser Pro Gly Ala Asp Gly Pro
                965                 970                 975

Pro Gly Arg Asp Gly Ala Ala Gly Val Lys Gly Asp Arg Gly Glu Thr
            980                 985                 990

Gly Ala Val Gly Ala Pro Gly Ala Pro Gly Pro Pro Gly Ser Pro Gly
        995                 1000                1005

Pro Ala Gly Pro Thr Gly Lys Gln Gly Asp Arg Gly Glu Ala Gly Ala
    1010                1015                1020

Gln Gly Pro Met Gly Pro Ser Gly Pro Ala Gly Ala Arg Gly Ile Gln
1025                1030                1035                1040

Gly Pro Gln Gly Pro Arg Gly Asp Lys Gly Glu Ala Gly Glu Pro Gly
                1045                1050                1055

Glu Arg Gly Leu Lys Gly His Arg Gly Phe Thr Gly Leu Gln Gly Leu
            1060                1065                1070

Pro Gly Pro Pro Gly Pro Ser Gly Asp Gln Gly Ala Ser Gly Pro Ala
        1075                1080                1085

Gly Pro Ser Gly Pro Arg Gly Pro Pro Gly Pro Val Gly Pro Ser Gly
    1090                1095                1100

Lys Asp Gly Ala Asn Gly Ile Pro Gly Pro Ile Gly Pro Pro Gly Pro
1105                1110                1115                1120

Arg Gly Arg Ser Gly Glu Thr Gly Pro Ala Gly Pro Pro Gly Asn Pro
                1125                1130                1135

Gly Pro Pro Gly Pro Pro Gly Pro Pro Gly Pro Gly Ile Asp Met Ser
            1140                1145                1150

Ala Phe Ala Gly Leu Gly Pro Arg Glu Lys Gly Pro Asp Pro Leu Gln
        1155                1160                1165

Tyr Met Arg Ala Asp Gln Ala Ala Gly Gly Leu Arg Gln His Asp Ala
    1170                1175                1180

Glu Val Asp Ala Thr Leu Lys Ser Leu Asn Asn Gln Ile Glu Ser Ile
1185                1190                1195                1200

Arg Ser Pro Glu Gly Ser Arg Lys Asn Pro Ala Arg Thr Cys Arg Asp
                1205                1210                1215

Leu Lys Leu Cys His Pro Glu Trp Lys Ser Gly Asp Tyr Trp Ile Asp
            1220                1225                1230

Pro Asn Gln Gly Cys Thr Leu Asp Ala Met Lys Val Phe Cys Asn Met
        1235                1240                1245

Glu Thr Gly Glu Thr Cys Val Tyr Pro Asn Pro Ala Asn Val Pro Lys
    1250                1255                1260

Lys Asn Trp Trp Ser Lys Ser Lys Glu Lys His Ile Trp Phe
1265                1270                1275                1280

Gly Glu Thr Ile Asn Gly Gly Phe His Phe Ser Tyr Gly Asp Asp Asn
                1285                1290                1295

Leu Ala Pro Asn Thr Ala Asn Val Gln Met Thr Phe Leu Arg Leu Leu
            1300                1305                1310

Ser Thr Glu Gly Ser Gln Asn Ile Thr Tyr His Cys Lys Asn Ser Ile
        1315                1320                1325
```

```
Ala Tyr Leu Asp Glu Ala Ala Gly Asn Leu Lys Lys Ala Leu Leu Ile
            1330                1335                1340

Gln Gly Ser Asn Asp Val Glu Ile Arg Ala Glu Gly Asn Ser Arg Phe
1345                1350                1355                1360

Thr Tyr Thr Ala Leu Lys Asp Gly Cys Thr Lys His Thr Gly Lys Trp
                1365                1370                1375

Gly Lys Thr Val Ile Glu Tyr Arg Ser Gln Lys Thr Ser Arg Leu Pro
            1380                1385                1390

Ile Ile Asp Ile Ala Pro Met Asp Ile Gly Pro Glu Gln Glu Phe
            1395                1400                1405

Gly Val Asp Ile Gly Pro Val Cys Phe Leu
            1410                1415

(2) INFORMATION FOR SEQ ID NO:21:

(i) SEQUENCE CHARACTERISTICS:
        (A) LENGTH: 1078 amino acids
        (B) TYPE: amino acid
        (D) TOPOLOGY: linear (ii) MOLECULE TYPE: protein (vi) ORIGINAL SOURCE:
         (A) ORGANISM: Homo sapiens (vii) IMMEDIATE SOURCE:
         (B) CLONE: COLLAGEN ALPHA 1 (III)

(xi) SEQUENCE DESCRIPTION: SEQ ID NO:21:

Gln Asn Tyr Ser Pro Gln Tyr Asp Ser Tyr Asp Val Lys Ser Gly Gly
1               5                   10                  15

Val Ala Val Gly Gly Leu Ala Gly Tyr Pro Gly Pro Ala Gly Pro Pro
            20                  25                  30

Gly Pro Pro Gly Pro Pro Gly Thr Ser Gly His Pro Gly Ser Pro Gly
            35                  40                  45

Ser Pro Gly Tyr Gln Gly Pro Pro Gly Glu Pro Gly Gln Ala Gly Pro
        50                  55                  60

Ser Gly Pro Pro Gly Pro Pro Gly Ala Ile Gly Pro Ser Gly Pro Ala
65                  70                  75                  80

Gly Lys Asp Gly Glu Ser Gly Arg Pro Gly Arg Pro Gly Asp Arg Gly
                85                  90                  95

Leu Pro Gly Pro Pro Gly Ile Lys Gly Pro Ala Gly Ile Pro Gly Phe
            100                 105                 110

Pro Gly Met Lys Gly His Arg Gly Phe Asp Gly Arg Asn Gly Glu Lys
            115                 120                 125

Gly Glu Thr Gly Ala Pro Gly Leu Lys Gly Glu Asn Gly Leu Pro Gly
        130                 135                 140

Glu Asn Gly Ala Pro Gly Pro Met Gly Pro Arg Gly Ala Pro Gly Glu
145                 150                 155                 160

Arg Gly Arg Pro Gly Leu Pro Gly Ala Ala Gly Ala Arg Gly Asn Asp
                165                 170                 175

Gly Ala Arg Gly Ser Asp Gly Gln Pro Gly Pro Pro Gly Pro Pro Gly
            180                 185                 190

Thr Ala Gly Phe Pro Gly Ser Pro Gly Ala Lys Gly Glu Val Gly Pro
            195                 200                 205

Ala Gly Ser Pro Gly Ser Asn Gly Ala Pro Gly Gln Arg Gly Glu Pro
        210                 215                 220
```

-continued

Gly Pro Gln Gly His Ala Gly Ala Gln Gly Pro Pro Gly Pro Pro Gly
225                 230                 235                 240

Ile Asn Gly Ser Pro Gly Gly Lys Gly Glu Met Gly Pro Ala Gly Ile
            245                 250                 255

Pro Gly Ala Pro Gly Leu Met Gly Ala Arg Gly Pro Pro Gly Pro Ala
            260                 265                 270

Gly Ala Asn Gly Ala Pro Gly Leu Arg Gly Gly Ala Gly Glu Pro Gly
        275                 280                 285

Lys Asn Gly Ala Lys Gly Glu Pro Gly Pro Arg Gly Glu Arg Gly Glu
    290                 295                 300

Ala Gly Ile Pro Gly Val Pro Gly Ala Lys Gly Glu Asp Gly Lys Asp
305                 310                 315                 320

Gly Ser Pro Gly Asp Pro Gly Ala Asn Gly Leu Pro Gly Ala Ala Gly
            325                 330                 335

Glu Arg Gly Ala Leu Gly Ser Arg Gly Pro Ala Gly Pro Asn Gly Ile
            340                 345                 350

Pro Gly Glu Lys Gly Pro Ala Gly Glu Arg Gly Ala Pro Gly Pro Ala
        355                 360                 365

Gly Pro Arg Gly Ala Ala Gly Glu Pro Gly Arg Asp Gly Val Pro Gly
    370                 375                 380

Gly Pro Gly Met Arg Gly Met Pro Gly Ser Pro Gly Gly Pro Gly Ser
385                 390                 395                 400

Asp Gly Lys Pro Gly Pro Pro Gly Ser Gln Gly Glu Ser Gly Arg Pro
            405                 410                 415

Gly Pro Pro Gly Pro Ser Gly Pro Arg Gly Gln Pro Gly Val Met Gly
            420                 425                 430

Phe Pro Gly Pro Lys Gly Asn Asp Gly Ala Pro Gly Lys Asn Gly Glu
        435                 440                 445

Arg Gly Gly Pro Gly Gly Pro Gly Pro Gln Gly Pro Pro Gly Lys Asn
    450                 455                 460

Gly Glu Tyr Gly Pro Gln Gly Pro Pro Gly Pro Thr Gly Pro Gly Gly
465                 470                 475                 480

Asp Lys Gly Asp Thr Gly Pro Arg Gly Pro Gln Gly Leu Gln Gly Leu
            485                 490                 495

Pro Gly Thr Gly Gly Pro Pro Gly Glu Asn Glu Lys Pro Gly Glu Pro
            500                 505                 510

Gly Pro Lys Gly Glu Ala Gly Ala Pro Gly Ala Pro Gly Gly Lys Gly
        515                 520                 525

Asp Ala Gly Ala Pro Gly Glu Arg Gly Pro Pro Gly Leu Ala Gly Ala
    530                 535                 540

Pro Gly Leu Arg Gly Gly Ala Gly Pro Pro Gly Pro Glu Gly Gly Lys
545                 550                 555                 560

Gly Ala Ala Gly Pro Pro Gly Pro Pro Gly Ala Ala Gly Thr Pro Gly
            565                 570                 575

Leu Gln Gly Met Pro Gly Glu Arg Gly Gly Leu Gly Ser Pro Gly Pro
            580                 585                 590

Lys Gly Asp Lys Gly Glu Pro Gly Gly Pro Gly Ala Asp Gly Val Pro
        595                 600                 605

Gly Lys Asp Gly Pro Arg Gly Pro Thr Gly Pro Ile Gly Pro Pro Gly
    610                 615                 620

Pro Ala Gly Gln Pro Gly Asp Lys Gly Glu Gly Gly Ala Pro Gly Leu
625                 630                 635                 640

Pro Gly Ile Ala Gly Pro Arg Gly Ser Pro Gly Glu Arg Gly Glu Thr

-continued

```
                        645                 650                 655
Gly Pro Pro Gly Pro Ala Gly Phe Pro Gly Ala Pro Gly Gln Asn Gly
                    660                 665                 670
Glu Pro Gly Gly Lys Gly Glu Arg Gly Ala Pro Gly Glu Lys Gly Glu
                675                 680                 685
Gly Gly Pro Pro Gly Val Ala Val Pro Pro Gly Ser Gly Pro Ala
            690                 695                 700
Gly Pro Pro Gly Pro Gln Gly Val Lys Gly Glu Arg Gly Ser Pro Gly
705                 710                 715                 720
Gly Pro Gly Ala Ala Gly Phe Pro Gly Ala Arg Gly Leu Pro Gly Pro
                725                 730                 735
Pro Gly Ser Asn Gly Asn Pro Gly Pro Pro Gly Pro Ser Gly Ser Pro
                740                 745                 750
Gly Lys Asp Gly Pro Pro Gly Pro Ala Gly Asn Thr Gly Ala Pro Gly
                755                 760                 765
Ser Pro Gly Val Ser Gly Pro Lys Gly Asp Ala Gly Gln Pro Gly Glu
                770                 775                 780
Lys Gly Ser Pro Gly Ala Gln Gly Pro Pro Gly Ala Pro Gly Pro Leu
785                 790                 795                 800
Gly Ile Ala Gly Ile Thr Gly Ala Arg Gly Leu Ala Gly Pro Pro Gly
                805                 810                 815
Met Pro Gly Pro Arg Gly Ser Pro Gly Pro Gln Gly Val Lys Gly Glu
                820                 825                 830
Ser Gly Lys Pro Gly Ala Asn Gly Leu Ser Gly Glu Arg Gly Pro Pro
                835                 840                 845
Gly Pro Gln Gly Leu Pro Gly Leu Ala Gly Thr Ala Gly Glu Pro Gly
                850                 855                 860
Arg Asp Gly Asn Pro Gly Ser Asp Gly Leu Pro Gly Arg Asp Gly Ser
865                 870                 875                 880
Pro Gly Gly Lys Gly Asp Arg Gly Glu Asn Gly Ser Pro Gly Ala Pro
                885                 890                 895
Gly Ala Pro Gly His Pro Gly Pro Pro Gly Pro Val Gly Pro Ala Gly
                900                 905                 910
Lys Ser Gly Asp Arg Gly Glu Ser Gly Pro Ala Gly Pro Ala Gly Ala
                915                 920                 925
Pro Gly Pro Ala Gly Ser Arg Gly Ala Pro Gly Pro Gln Gly Pro Arg
                930                 935                 940
Gly Asp Lys Gly Glu Thr Gly Glu Arg Gly Ala Ala Gly Ile Lys Gly
945                 950                 955                 960
His Arg Gly Phe Pro Gly Asn Pro Gly Ala Pro Gly Ser Pro Gly Pro
                965                 970                 975
Ala Gly Gln Gln Gly Ala Ile Gly Ser Pro Gly Pro Ala Gly Pro Arg
                980                 985                 990
Gly Pro Val Gly Pro Ser Gly Pro Pro Gly Lys Asp Gly Thr Ser Gly
                995                 1000                1005
His Pro Gly Pro Ile Gly Pro Pro Gly Pro Arg Gly Asn Arg Gly Glu
            1010                1015                1020
Arg Gly Ser Glu Gly Ser Pro Gly His Pro Gly Gln Ser Gly Pro Pro
1025                1030                1035                1040
Gly Pro Pro Gly Ala Pro Gly Pro Cys Cys Gly Gly Val Gly Ala Pro
                1045                1050                1055
```

―continued

```
Ala Ile Ala Gly Ile Gly Ala Glu Lys Ala Gly Gly Phe Ala Pro Tyr
        1060            1065            1070

Tyr Gly Asp Glu Pro Met
        1075
```

APPENDIX A collagen alpha 1(I) chain precursor-Human (fragments)
Homo sapiens (man) SEQ. ID. NO. 18.
   Number of residue = 1341

```
            5          10          15          20          25          30
   1 M F S F V D L R L L L L L A A T A L L T H G Q E E G Q V E G

31 Q D E D I P P I T C V Q N G L R Y H D R D V W K P E P C Q I

61 C V C D N G K V L C D D V I C D E T K N C P G A E V P E G E

91 C C P V C P D G S E S P T D Q E T T G V E G P K G D T G P R

121 G P R G P A G P P G R D G I P G Q P G L P G P P G P P G P P

151 G P P G L G G N F A P Q L S Y G Y D E K S T G G I S V P G P

181 M(G P S G P R G L P G P P G A P G P Z G F Z G P P G Z P G Z

211 P G A S G P)M(G P R G P P G P P G K B G B B G Z A G K P G R

241 P G Z R G P P G P Z G A R G L P G T A G L P)G M K G H R(G F

271 S G L B G A K G B A G P A G P K G Z P G S P G Z B G A P G Z)

301 M/G P P G P K G N S G E P G A P G S K G D T G A K G E P G P

331 V G V Q G P P G P A G E E G K R G A R G E P G P T G L P G P

361 P G E R G G P G S R G F P G A D G V A G P K G P A G E R G S

391 P G P A G P K G S P G E A G R P G E A G L P G A K G L T G S

421 P G S P G P D G K T G P P G P A G Q D G R P G P P G P P G A

451 R G Q A G V M G F P G P K G A A G E P G K A G E R G V P G P

481 P G A V G P A G K D G E A G A Q G P P G P A G P A G E R G E

511 Q G P A G S P G F Q G L P G P A G P P G E A G K P G E Q G V

541 P G D L G A P G P S G A R G E R G F P G E R G V Q G P P G P

571 A G P R G A N G A P G N D G A K G D A G A P G A P G S Q G A

601 P G L Q G M P G E R G A A G L P G P K G D R G D A G P K G A

631 D G S P G K D G V R G L T G P I G P P G P A G A P G D K G E

661 S G P S G P A G P T G A R G A P G D R G E P G P P G P A G F

691 A G P P G A D G Q P G A K G E P G D A G A K G D A G P P G P

721 A G P A G P P G P I G N V G A P G A K G A R G S A G P P G A

751 T G F P G A A G R V G P P G P S G N A G P P G P P G P A G K

781 E G G K G P R G E T G P A G R P G E V G P P G P P G P A G E

811 K G S P G A D G P A G A P G T P G P Q G I A G Q R G V V G L

841 P G Q R G E R G F P G L P G P S G E P G K Q G P S G A S G E

871 R G P P G P M G P P G L A G P P G E S G R E G A P G A E G S

901 P G R D G S P G A K G D R G E T G P A G P P G A X G A X G A
```

-continued

```
 931 P G P V G P A G K S G D R G E T G P A G P A G P V G P A G A
 961 R G P A G P Q G P R G D K G E T G E Q G D R G I K G H R G F
 991 S G L Q G P P G P P G S P G E Q G P S G A S G P A G P R G P
1021 P G S A G A P G K D G L N G L P G P I G P P G P R G R T G D
1051 A G P V G P P G P P G P P G P P G P P S A G F D F S F L P Q
1081 P P Q E K A H D G G R Y Y R A D D A N V V R D R D L E V D T
1111 T L K S L S Q Q I E N I R S P E G X R K N P A R T C R D L K
1141 M C H S D W K S G E Y W I D P N Q G C N L D A I K V F C N M
1171 E T G E T C V Y P T Q P S V A Q K N W Y I S K N P K D K R H
1201 V W F G E S M T D G F Q F E Y G G Q G S D P A D V A I Q L T
1231 F L R L M S T E A S Q N I T Y H C K N S V A Y M D Q Q T G N
1261 L K K A L L L X G S N E I E I R A E G N S R F T Y S V T V D
1291 G C T S H T G A W G K T V I E Y K T T K S S R L P I I D V A
1321 P L D V G A P D Q E F G F D V G P V C F L
```

Sequence of collagen alpha 1(I) chanin precursor prepared from:

Chu, M.L., de Wet, W., Bernard, M., ding, J.F., Morabito, M., Myers, J., Williams, C., and Ramirez, F., Nature 310, translated from the DNA sequence)

Click, E.M., and Bornstein, P., Biochemistry 9, 4699-4706, 1970 (Human skin, CNBr0-1, CNBr2, CNBr4, CNBr5, partial sequence of residue 162-301)

Morgan, P.H., Jacobs, H.G., Segrest. J.P., and Cunningham, L.W., J. Biol. Chem. 245, 5042-5048, 1970 (Human skin, sequence of residues 263-268)

Bernard, M.P., Chu, M.L., Myers, J.C., Ramirez, F., Eikenberry, E.F., and Prockop, D.J., Biochemistry 22, 5213-5223, 1983 (Sequence of residues 302-1341 translated from the mRNA sequence)

Procollagen alpha 2(I) chain precursor Homo sapiens (man) SEQ. ID. NO. 19.

Number of residues = 1366

```
               5         10         15         20         25         30
   1 M L S F V D T R T L L L L A V T L C L A T C Q S L Q E E T V
  31 R K G P A G D R G P R G E R G P P G P P G R D G E D G P T G
  61 P P G P P G P P G P P G L G G N F A A Q Y D G K G V G L G P
  91 G P M G L M G P R G P P G A A G A P G P Q G F Q G P A G E P
 121 G E P G Q T G P A G A R G P A G P P G K A G E D G H P G K P
 151 G R P G E R G V V G P Q G A R G F P G T P G L P G F K G I R
 181 G H N G L D G L K G Q P G A P G V K G E P G A P G E N G T P
 211 G Q T G A R G L P G E R G R V G A P G P A G A R G S D G S V
 241 G P V G P A G P N G S A G P P G F P G A P G P K G E I G A V
 271 G N A G P T G P A G P R G E V G L P G L S G P V G P P G N P
 301 G A N G L T G A K G A A G L P G V A G A P G L P G P R G I P
 331 G P P G A A G T T G A R G L V G E P G P A G S K G E S G N K
 361 G E P G S A G P Q G P P G P S G E E G K R G P N G E A G S A
 391 G P P G P P G L R G S P G S R G L P G A D G R A G V M G P P
 421 G S R G A S G P A G V R G P N G D A G R P G E P G L M G P R
 451 G L P G S P G N I G P A G K E G P V G L P G I D G R P G P I
```

```
-continued
 481 G P V G A R G E P G N I G F P G P K G P T G D P G K N G D K

511 G H A G L A G A R G A P G P D G N N G A Q G P P G P Q G V Q

541 G G K G E Q G P A G P P G F Q G L P G P S G P A G E V G K P

571 G E R G L H G E F G L P G P A G P R G E R G P P G E S G A A

601 G P T G P I G S R G P S G P P G P D G N K G E P G V V G A V

631 G T A G P S G P S G L P G E R G A A G I P G G K G E K G E P

661 G L R G E I G N P G R D G A R G A H G A V G A P G P A G A T

691 G D R G E A G A A G P A G P A G P R G S P G E R G E V G P A

721 G P N G F A G P A G A A G Q P G A K G E R G G K G P K G E N

751 G V V G P T G P V G A A G P A G P N G P P G P A G S R G D G

781 G P P G M T G F P G A A G R T G P P G P S G I S G P P G P P

811 G P A G K E G L R G P R G D Q G P V G R T G E V G A V G P P

841 G F A G E K G P S G E A G T A G P P G T P G P Q G L L G A P

871 G I L G L P G S R G E R G L P G V A G A V G E P G P L G I A

901 G P P G A R G P P G A V G S P G V N G A P G E A G R D G N P

931 G N D G P P G R D G Q P G H K G E R G Y P G N I G P V G A A

961 G A P G P H G P V G P A G K H G N R G E T G P S G P V G P A

991 G A V G P R G P S G P Q G I R G D K G E P G E K G P R G L P

1021 G F K G H N G L Q G L P G I A G H H G D Q G A P G S V G P A

1051 G P R G P A G P S G P A G K D G R T G H P G T V G P A G I R

1081 G P Q G H Q G P A G P P G P P G P P G P P G V S G G G Y D F

1111 G Y D G D F Y R A D Q P R S A P S L R P K D Y E V D A T L K

1141 S L N N Q I E T L L T P E G S R K N P A R T C R D L R L S H

1171 P E W S S G Y Y W I D P N Q G C T M E A I K V Y C D F P T G

1201 E T C I R A Q P E N I P A K N W Y R S S K D K K H V W L G E

1231 T I N A G S Q F E Y N V E G V T S K E M A T Q L A F M R L L

1261 A N Y A S Q N I T Y H C K N S I A Y M D E E T G N L K K A V

1291 I L Q G S N D V E L V A E G N S R F T Y T V L V D G C S K K

1321 T N E W G K T I I E Y K T N K P S R L P F L D I A P L D I G

1351 G A D H E F F V D I G P V C F K
```

Sequence of procollagen alpha 2(I) chain precursor prepared from:

de Wet, W., Bernard, M., Benson-Chanda, V., Chu, M.L., Dickson, L., Weil, D., and Ramirez, F., J. Biol. Chem. 262, 16032-16036, 1987 (Sequence translated from the mRNA sequence)

Title: Organization of the human pro-alpha-2(I) collagen gene.

Collagen alpha 1(II) chain precursor Homo sapiens (man) SEQ. ID. NO. 20.

```
  1  MIRLGAPQSL VLLTLLVAAV LRCQGQDVRQ PGPKGQKGEP GDIKDIVGPK

51  GPPGPQGPAG EQGPRGDRGD KGEKGAPGPR GRDGEPGTLG NPGPPGPPGP

101  PGPPGLGGNF AAQMAGGFDE KAGGAQLGVM QGPMGPMGPR GPPGPAGAPG

151  PQGFQGNPGE PGEPGVSGPM GPRGPPGPPG KPGDDGEAGK PGKAGERGPP
```

```
-continued
 201   GPQGARGFPG  TPGLPGVKGH  RGYPGLDGAK  GEAGAPGVKG  ESGSPGENGS
 251   PGPMGPRGLP  GERGRTGPAG  AAGARGNDGQ  PGPAGPPGPV  GPAGGPGFPG
 301   APGAKGEAGP  TGARGPEGAQ  GPRGEPGTPG  SPGPAGASGN  PGTDGIPGAK
 351   GSAGAPGIAG  APGFPGPRGP  PDPQGATGPL  GPKGQTGKPG  IAGFKGEQGP
 401   KGEPGPAGPQ  GAPGPAGEEG  KRGARGEPGG  VGPIGPPGER  GAPGNRGFPG
 451   QDGLAGPKGA  PGERGPSGLA  GPKGANGDPG  RPGEPGLPGA  RGLTGRPGDA
 501   GPQGKVGPSG  APGEDGRPGP  PGPQGARGQP  GVMGFPGPKG  ANGEPGKAGE
 551   KGLPGAPGLR  GLPGKDGETG  AEGPPGPAGP  AGERGEQGAP  GPSGFQGLPG
 601   PPGPPGEGGK  PGDQGVPGEA  GAPGLVGPRG  ERGFPGERGS  PGAQGLQGPR
 651   GLPGTPGTDG  PKGASGPAGP  PGAQGPPGLQ  GMPGERGAAG  IAGPKGDRGD
 701   VGEKGPEGAP  GKDGGRGLTG  PIGPPGPAGA  NGEKGEVGPP  GPAGSAGARG
 751   APGERGETGP  PGTSGIAGPP  GADGQPGAKG  EQGEAGQKGD  AGAPGPQGPS
 801   GAPGPQGPTG  VTGPKGARGA  QGPPGATGFP  GAAGRVGPPG  SNGNPGPPGP
 851   PGPSGKDGPK  GARGDSGPPG  RAGEPGLQGP  AGPPGEKGEP  GDDGPSGAEG
 901   PPGPQGLAGQ  RGIVGLPGQR  GERGFPGLPG  PSGEPGQQGA  PGASGDRGPP
 951   GPVGPPGLTG  PAGEPGREGS  PGADGPPGRD  GAAGVKGDRG  ETGAVGAPGA
1001   PGPPGSPGPA  GPTGKQGDRG  EAGAQGPMGP  SGPAGARGIQ  GPQGPRGDKG
1051   EAGEPGERGL  KGHRGFTGLQ  GLPGPPGPSG  DQGASGPAGP  SGPRGPPGPV
1101   GPSGKDGANG  IPGPIGPPGP  RGRSGETGPA  GPPGNPGPPG  PPGPPGPGID
1151   MSAFAGLGPR  EKGPDPLQYM  RADQAAGGLR  QHDAEVDATL  KSLNNQIESI
1201   RSPEGSRKNP  ARTCRDLKLC  HPEWKSGDYW  IDPNQGCTLD  AMKVFCNMET
1251   GETCVYPNPA  NVPKKNWWSS  KSKEKKHIWF  GETINGGFHF  SYGDDNLAPN
1301   TANVQMTFLR  LLSTEGSQNI  TYHCKNSIAY  LDEAAGNLKK  ALLIQGSNDV
1351   EIRAEGNSRF  TYTALKDGCT  KHTGKWGKTV  IEYRSQKTSR  LPIIDIAPMD
1401   IGGPEQEFGV  DIGPVCFL
```

Sequence of collagen alpha 1(II) chain precursor prepared from:

Su, M.W., Lee, B., Ramirez, F., Machado, M., and Horton, W. Nucleic Acids Res. 17, 9473, 1989 Nucleotide sequence of the full length cDNA encoding for human type II procollagen.

Baldwin, C.T., Reginato, A.M., Smith, C., Jimenez, S.A., and Prockop, D.J., Biochem. J. 262, 521-528, 1989 Structure of cDNA clones coding for human type II procollagen. The alpha-1(II) chain is more similar to the alpha-1(I) chain than two other alpha chains of fibrillar collagens.

Ala-Kokko, L., Baldwin, C.T., Moskowitz, R.W., and Prockop, D.J. Proc. Natl. Acad. Sci. U.S.S. 87, 6565-6568, 1990 Single base mutation in the type II procollagen gene (COL2a1) as a cause of primary osteoarthritis associated with a mild chondrodysplasia.

Ramirez, F. submitted to the EMBL Data Library, December 1988 Reference number: S04892

Vikkula, M., and Peltonen, L. FEBS Lett. 250, 171-174, 1989 Structural analyses of the polymorphic area in type II collagen gene.

Collagen alpha 1(III) chain precursor Homo sapiens (man) SEQ. ID. NO. 21.

Number of residues = 1078

```
       5         10        15        20        25        30
  1/Q N Y S P Q Y D S Y D V K S G G V A V G G L A G Y P G P A G

31 P P G P P G P P G T S G H P G S P G S P G Y Q G P P G E P G

61 Q A G P S G P P G P P G A I G P S G P A G K D G E S G R P G

91 R P G D R G L P G P P G I K G P A G I P G F P G M K G H R G

121 F D G R N G E K G E T G A P G L K G E N G L P G E N G A P G

151 P M G P R G A P G E R G R P G L P G A A G A R G N D G A R G

181 S D G Q P G P P G P P G T A G F P G S P G A K G E V G P A G

211 S P G S N G A P G Q R G E P G P Q G H A G A Q G P P G P P G

241 I N G S P G G K G E M G P A G I P G A P G L M G A R G P P G

271 P A G A N G A P G L R G G A G E P G K N G A K G E P G P R G

301 E R G E A G I P G V P G A K G E D G K D G S P G D P G A N G

331 L P G A A G E R G A L G S R G P A G P N G I P G E K G P A G

361 E R G A P G P A G P R G A A G E P G R D G V P G G P G M R G

391 M P G S P G G P G S D G K P G P P G S Q G E S G R P G P P G

421 P S G P R G Q P G V M G F P G P K G N D G A P G K N G E R G

451 G P G G P G P Q G P P G K N G E Y G P Q G P P G P T G P G G

481 D K G D T G P R G P Q G L Q G L P G T G G P P G E N G K P G

511 E P G P K G E A G A P G A P G G K G D A G A P G E R G P P G

541 L A G A P G L R G G A G P P G P E G G K G A A G P P G P P G

571 A A G T P G L Q G M P G E R G G L G S P G P K G D K G E P G

601 G P G A D G V P G K D G P R G P T G P I G P P G P A G Q P G

631 D K G E G G A P G L P G I A G P R G S P G E R G E T G P P G

661 P A G F P G A P G Q N G E P G G K G E R G A P G E K G E G G

691 P P G V A G P P G G S G P A G P P G P Q G V K G E R G S P G

721 G P G A A G F P G A R G L P G P P G S N G N P G P P G P S G

751 S P G K D G P P G P A G N T G A P G S P G V S G P K G D A G

781 Q P G E K G S P G A Q G P P G A P G P L G I A G I T G A R G

811 L A G P P G M P G P R G S P G P Q G V K G E S G K P G A N G

841 L S G E R G P P G P Q G L P G L A G T A G E P G R D G N P G

871 S D G L P G R D G S P G G K G D R G E N G S P G A P G A P G

901 H P G P P G P V G P A G K S G D R G E S G P A G P A G A P G

931 P A G S R G A P G P Q G P R G D K G E T G E R G A A G I K G

961 H R G F P G N P G A P G S P G P A G Q Q G A I G S P G P A G

991 P R G P V G P S G P P G K D G T S G H P G P I G P P G P R G

1021 N R G E R G S E G S P G H P G Q S G P P G P P G A P G P C C

1051 G G V G A P A I A G I G A E K A G G F A P Y Y G D E P M/
```

Sequence of collagen alpha 1(III) chain precursor prepared from:

Janeczko, R.A., and Ramirez, F., Nucleic Acids Res., 17, 6742, 1989 Nucleotide and amino acid sequences of the entire human alpha-1(III) collagen.

What is claimed is:
1. A method of assaying type I collagen fragments in a body fluid sample, comprising:
    (a) contacting the body fluid with a synthetic peptide consisting essentially of the type I collagen α(I) amino acid sequence Glu-Lys-Ala-His-Asp-Gly-Gly-Arg

(SEQ ID NO: 2), and an immunological binding partner immunoreactive with said amino acid sequence, wherein the collagen fragments compete with said synthetic peptide for binding with the immunological binding partner; and (b) quantifying the amount of collagen fragments in the sample by measuring the amount of binding of said immunological binding partner with said collagen fragments.

2. The method of claim 1, wherein the immunological binding partner is a monoclonal antibody or an immunologically active fragment thereof.

3. The method of claim 1, wherein the body fluid is urine.

4. The method of claim 1, wherein the sample is obtained from a post-menopausal woman.

5. The method of claim 1, wherein the amount of type I collagen fragments in the body fluid sample is quantified with reference to the amount of binding between the immunological binding partner and one or more standard samples.

6. A method of diagnosing or monitoring osteoporosis in a test individual, comprising:

(a) contacting a body fluid sample of the test individual with a synthetic peptide consisting essentially of the type I collagen α(I) amino acid sequence Glu-Lys-Ala-His-Asp-Gly-Gly-Arg (SEQ ID NO: 2), and an immunological binding partner immunoreactive with said amino acid sequence, wherein the collagen fragments compete with the synthetic peptide for binding with the immunological binding partner;

(b) quantifying the amount of collagen fragments in the sample by measuring the amount of binding of said immunological binding partner with said collagen fragments; and (c) comparing the amount quantified in step (b) to the amount of collagen fragments quantified in a body fluid sample of a normal individual, whereby osteoporosis is indicated by a greater amount of collagen fragments quantified in step (b) relative to the amount detected in the body fluid sample of the normal individual.

7. The method of claim 6, wherein the body fluid is urine.

8. The method of claim 6 or 7, wherein the test individual is a post-menopausal woman.

9. An immunological binding partner that binds to the type I collagen α(I) amino acid sequence Glu-Lys-Ala-His-Asp-Gly-Gly-Arg (SEQ ID NO: 2), wherein said immunological binding partner is raised against a synthetic peptide consisting essentially of said amino acid sequence.

10. The immunological binding partner of claim 9 that is a monoclonal antibody or immunologically active fragment thereof.

11. A cell line which produces a monoclonal antibody that binds to the type I collagen α(I) amino acid sequence Glu-Lys-Ala-His-Asp-Gly-Gly-Arg (SEQ ID NO: 2), wherein said immunological binding partner is raised against a synthetic peptide consisting essentially of said sequence.

12. A test kit for assaying type I collagen fragments in a body fluid sample, comprising the immunological binding partner of claim 9.

13. A test kit for assaying type I collagen fragments in a body fluid sample, comprising the monoclonal antibody of claim 10.

* * * * *